United States Patent
Neven et al.

(10) Patent No.: US 8,772,265 B2
(45) Date of Patent: Jul. 8, 2014

(54) WATER SOLUBLE CURCUMIN COMPOSITIONS FOR USE IN ANTI-CANCER AND ANTI-INFLAMMATORY THERAPY

(75) Inventors: Philippe Neven, Nandrin (BE); Didier Serteyn, Tavier (BE); Jacques Delarge, Dolembreux-Sprimont (BE); Eva Scheer, legal representative, Dolembreux-Sprimont (BE); Robert Kiss, St Pieters Leeuw (BE); Veronique Mathieu, Brussels (BE); Didier Cataldo, Olne (BE); Natacha Rocks, La Calamine (BE)

(73) Assignees: Universite Libre de Bruxelles, Brussels (BE); Universite de Liege, Liege (BE)

( * ) Notice: Subject to any disclaimer, the term of this patent is extended or adjusted under 35 U.S.C. 154(b) by 311 days.

(21) Appl. No.: 12/995,126

(22) PCT Filed: May 26, 2009

(86) PCT No.: PCT/EP2009/056369
§ 371 (c)(1),
(2), (4) Date: Feb. 23, 2011

(87) PCT Pub. No.: WO2009/144220
PCT Pub. Date: Dec. 3, 2009

(65) Prior Publication Data
US 2011/0257126 A1 Oct. 20, 2011

Related U.S. Application Data

(60) Provisional application No. 61/057,078, filed on May 29, 2008.

(30) Foreign Application Priority Data

May 29, 2008 (EP) .................................... 08157160

(51) Int. Cl.
*A01N 43/04* (2006.01)
*A61K 31/715* (2006.01)
(52) U.S. Cl.
USPC ........................................................ 514/58
(58) Field of Classification Search
None
See application file for complete search history.

(56) References Cited

FOREIGN PATENT DOCUMENTS

| CN | 1 534 013 | 10/2004 |
|----|-----------|---------|
| CN | 1 543 933 | 11/2004 |
| EP | 1 018 340 | 7/2000 |
| JP | 06-009479 | 1/1994 |

OTHER PUBLICATIONS

Tonnesen et al. International Journal of Pharmaceutics 244 (2002) 127-135.*
Ishigami et al. J. Jpn. Soc. Colour Material, vol. 68, No. 6, pp. 331-336, 1995, English abstract.*
Anand et al. Mol. Pharmaceutics, 2007, 4 (6), 807-818, Nov. 2007.*
Baglole, et al. "Fluorescence Enhancement of Curcumin upon Inclusion into Parent and Modified Cyclodextrins," *Journal of Photochemistry and Photobiology*, vol. 173, No. 3, pp. 230-237, Jul. 5, 2005.
Tang, et al. "Study on the Supramolecular Interaction of Curcumin and β-cyclodextrin by Spectrophotometry and its Analytical Application," *Journal of Agricultural and Food Chemistry*, vol. 50, No. 6, pp. 1355-1359, Mar. 13, 2002.
International Search Report dated Aug. 24, 2009 and issued to international application No. PCT/EP2009/056369.

* cited by examiner

*Primary Examiner* — Layla Bland
(74) *Attorney, Agent, or Firm* — Knobbe, Martens, Olson & Bear LLP

(57) ABSTRACT

The present invention relates to the medical field. In a first aspect the present invention relates to novel water soluble cyclodextrin-curcumin complexes having a pharmacological activity, in particular an anti-tumor and/or anti-inflammatory activity, and improved physico-chemical properties. In a second aspect, the present invention relates to a method for preparation of said water soluble curcumin derivatives. The invention further relates in a third aspect to a pharmaceutical composition comprising an effective amount of said water soluble curcumin derivatives. In a fourth aspect, the present invention concerns the use of said water soluble cucumin derivatives as a medicament and the use of said water soluble curcumin derivatives for the preparation of a medicament for the treatment of cancer and inflammatory diseases. In a fifth aspect, the present invention relates to the use of a pharmaceutical composition comprising said water soluble curcumin derivatives in the treatment of cancer and inflammatory diseases and to a new pharmaceutical composition comprising said water soluble curcumin derivatives.

16 Claims, 22 Drawing Sheets

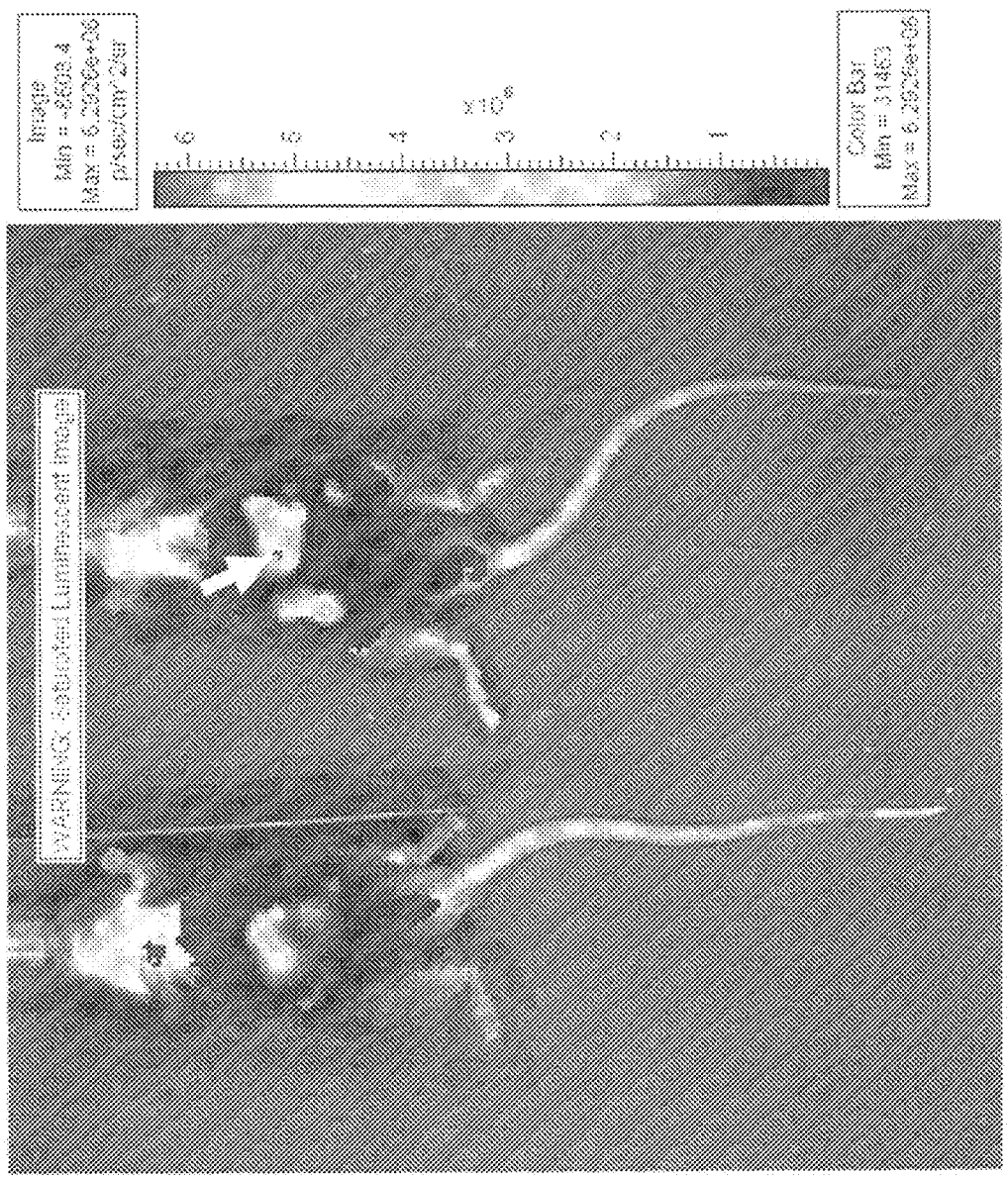

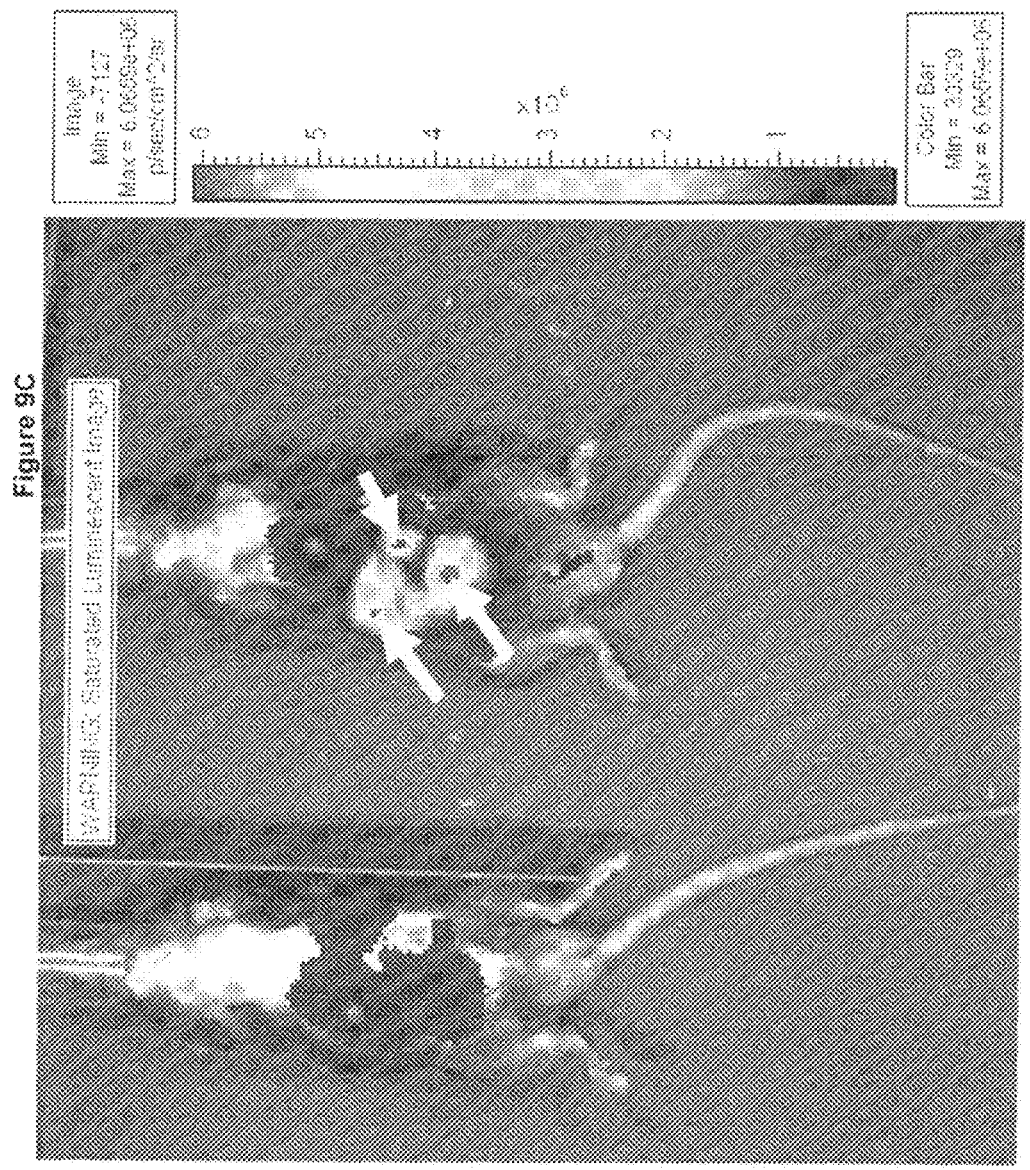

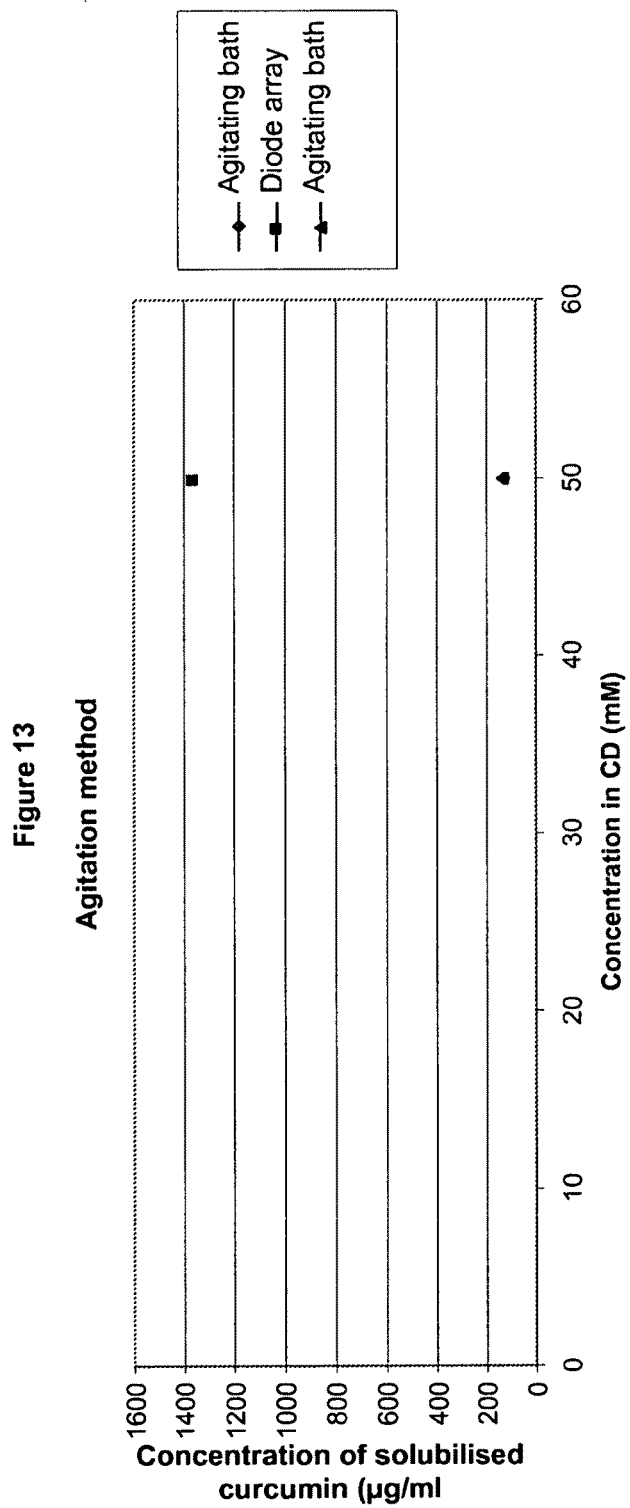

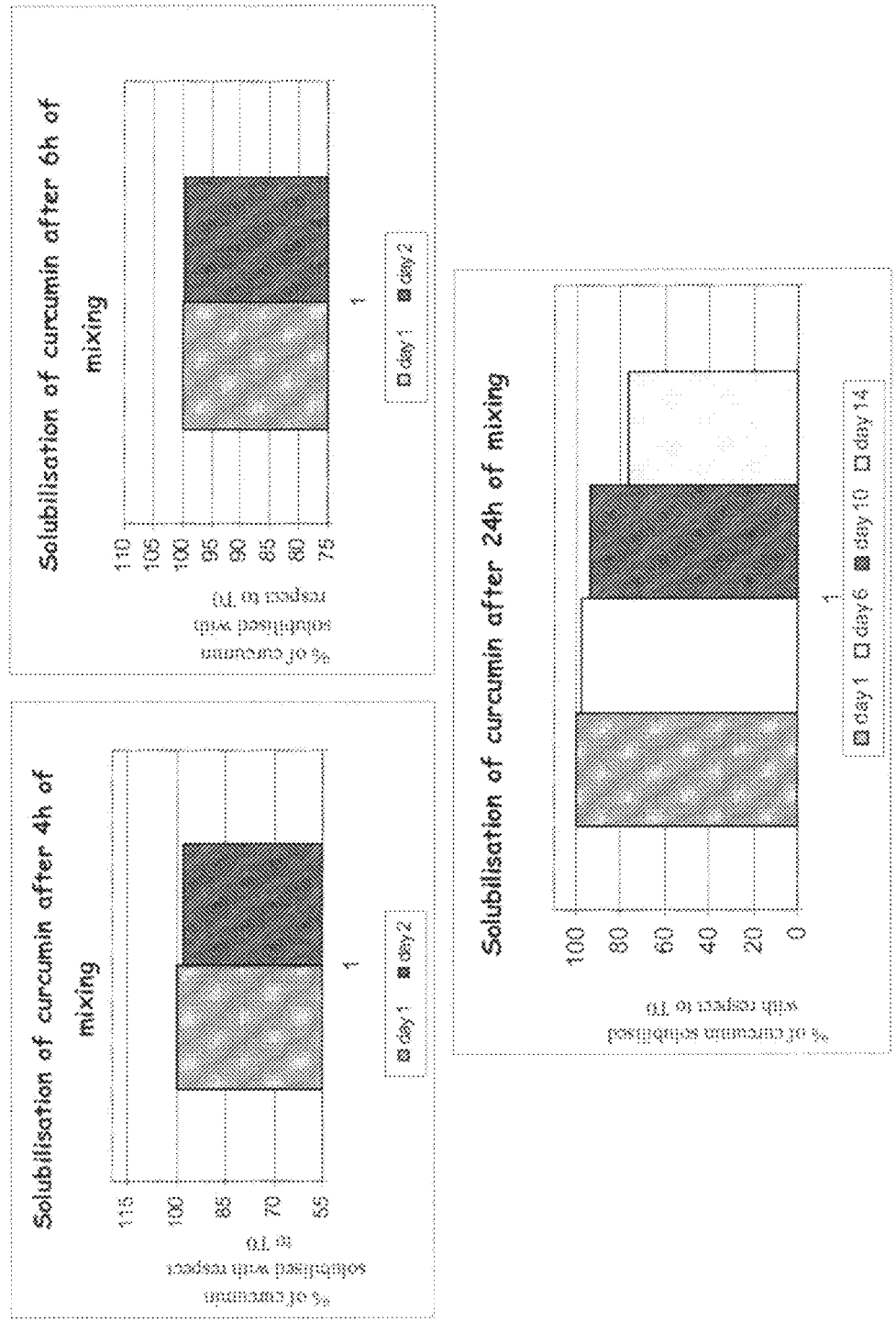

WATER SOLUBLE CURCUMIN COMPOSITIONS FOR USE IN ANTI-CANCER AND ANTI-INFLAMMATORY THERAPY

CROSS-REFERENCE TO RELATED APPLICATIONS

This application is the U.S. National Phase under 35 U.S.C. §371 of International Application PCT/EP2009/056369, filed May 26, 2009, which claims priority to EP 08157160.6, filed May 29, 2008 and U.S. Provisional Application No. 61/057,078 filed May 29, 2008.

FIELD OF THE INVENTION

The invention relates to the medical field, more precisely the field of anti-cancer and anti-inflammatory treatment using new water soluble curcumin compositions.

BACKGROUND OF THE INVENTION

Curcumin is the major curcuminoid of the Indian curry spice turmeric. Curcumin is known for its anti-oxidant, anti-arthritic, anti-amyloid and anti-inflammatory properties. In addition, over recent years, activity of curcumin against various types of cancer have been widely documented (Rao C. V. et al, Cancer Res. 55, 259-266, 1995, Kawamori et al, Cancer Res. 59, 597-601, 1999).

While curcumin exhibits promising anti-cancer and/or anti-inflammatory properties, one of its major drawbacks relates to its absorption, distribution and excretion in vivo. It has been described that blood levels of curcumin are always low after per os (oral) administration while they rise through intravenous injection. Besides that, it has been described that curcumin is totally metabolised in half an hour and that curcumin does not induce toxicity (Wahlström B. et al, Acta pharmacol. et toxicol. 43, 86-92, 1978; Pan M. H. et al, Drug Metabolism and Disposition, 27, 486-494, 1999, Ireson C. et al, Cancer Res. 61, 1058-1064, 2001).

Although the level of activity found for curcumin and curcuminoid derivatives was and continues to be of high interest, this administered material does have significant deficiencies which indicates the continuing need for curcumin-complexes with improved properties. In the first place, curcumin was found to be insoluble in the majority of usual solvents. In addition, the plasma concentrations of curcumin after per os administration are either undetectable or very weak whatever the dosage level. Also, it seems that curcumin is quickly reduced (tetrahydrocurcumin, hexahydrocurcumin, hexahydrocurcuminol) and/or transformed (glucuronides or sulphates) in vivo. Thus, while curcumin and curcuminoid derivatives show significant biological activity, they do not have physico-chemical properties suitable for further clinical development. The same shortcomings were observed for cyclodextrin complexes of curcuminoid derivatives as for salts of curcuminoid derivatives.

In addition, although the pre-clinical activity of anti-proliferative agents such as curcumin itself or curcuminoid derivatives against certain forms of cancers can be shown, improvement in tumour response rates, duration of response, decrease of toxicity and ultimately patient survival are still sought.

Clinical data has furthermore indicated that patients displaying pulmonary inflammatory diseases have a higher incidence of developing lung tumours. This suggests that a persistent pulmonary inflammation might alter the organ's properties to develop tumours, although the exact mechanisms connecting chronic inflammatory processes to cancer are not yet well known. Until today, no treatment for precancerous lesions in the lungs exists. There is also no treatment available which can stop or slow down the formation of lung cancer in patients displaying an inflammatory disease in the airways.

There is therefore an urgent need for identifying new active molecules displaying a potential interest for the treatment of inflammatory, precancerous or cancer diseases.

There is also a need in the art for improving the efficacy of anti-proliferative and anti-inflammatory treatments in humans and animals by providing suitable combinations of new drugs with conventional anti-neoplastic and/or anti-inflammatory agents.

In view of the above-mentioned shortcomings of most of the agents used today in hospitals to treat cancer patients or patients with inflammatory disease, of known curcumin and curcuminoid derivatives, of salts of curcuminoid derivatives and of cyclodextrin complexes of curcuminoid derivatives, there is a need in the art for new curcumin-derived compounds having enhanced physico-chemical properties and demonstrating a more promising activity/side effects balance.

The aim of the present invention was therefore to provide a new potential anti-proliferative and/or anti-inflammatory agent that is suitable for per os administration. Simultaneously, said new agents were evaluated for their ability to modulate pulmonary inflammation and/or lung cancer progression through trans-tracheal administration (e.g. inhalation).

Our findings suggest that new curcumin-derivatives of the present invention are interesting candidates for therapy against both proliferative and/or inflammatory disorders. Especially the increased solubility and prolonged stability of the curcumin-derivatives according to the invention and their surprising activity via per os administration is very interesting and unexpected.

SUMMARY OF THE INVENTION

The invention relates to methods and compounds for treating proliferative and/or inflammatory disorders. In particular, the invention provides water soluble and stable curcumin compositions or curcumin-derived compounds for treating proliferative and/or inflammatory disorders. In a preferred embodiment, the water soluble curcumin compounds of the invention are compounds of general formula I:

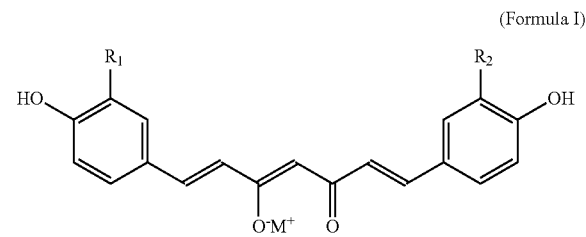

(Formula I)

wherein M is lysine or arginine and R1 and R2 are each independently selected from hydrogen, hydroxy or alkoxy, and/or stereoisomers thereof.

The preferred water soluble curcumin compounds of the invention are cyclodextrin complexes of the compounds of general formula I, and/or stereoisomers thereof.

In an even more preferred embodiment, the curcumin compounds of the invention are hydroxypropyl-beta-cyclodextrin (HP-beta-CD) or hydroxypropyl-gamma-cyclodextrin (HP-gamma-CD) complexes of the compounds of general formula I, i.e. the arginine or lysine salts of curcumin.

In the most preferred embodiment, the compound of the invention is a hydroxypropyl-beta-cyclodextrin complex of curcumin lysinate, called NDS27 hereinafter and a hydroxypropyl-gamma-cyclodextrin of curcumin lysinate, called NDS28 hereinafter.

Curcumin used in the preparation of the water soluble curcumin compound of the invention can be converted, resulting in the acylated derivative of curcumin or a derivative thereof or a glycosylated derivative.

The water soluble curcumin compounds of the invention can be lyophilised.

Alternatively, the water soluble curcumin compound according to the invention can be a cyclodextrin derivative of curcumin itself (i.e. not the lysine or arginine salt), preferably a beta or gamma-cyclodextrin derivative of curcumin, more preferably a gamma-cyclodextrin derivative of curcumin, most preferably HP-gamma-CD-curcumin.

The invention further provides pharmaceutical compositions comprising at least a therapeutically sufficient amount of the water soluble curcumin compounds of the invention as active ingredient and a pharmaceutically acceptable vehicle or carrier. Preferably, the therapeutically sufficient amount is comprised between 0.01 mg and 1000 mg per kilogram of body weight.

In a preferred embodiment, said pharmaceutical composition comprises the NDS27 and/or NDS28 composition as the active ingredient.

In a further embodiment, the pharmaceutical composition according to the invention has a pharmaceutically acceptable administration form selected from the group consisting of tablets, ills, capsules, suppositories, syrups, solutions, creams and sprays.

In an alternative embodiment, the pharmaceutical composition further comprises an adjuvant able to increase or regulate humoral and/or cellular response of the immune system against the active principle or against the vehicle or carrier so as to reduce or suppress side-effects or toxic effects associated to the active principle and/or the vehicle or carrier.

The invention further provides the use of the water soluble curcumin compound according to the invention or the pharmaceutical composition according to the invention in the manufacture of a medicament for treating proliferative disorders such as neoplasma, dysplasia, premalignant or precancerous lesions, abnormal cell growths, benign tumours, malignant tumours, cancer or metastasis; or inflammatory disorders such as pulmonary disorders, pneumonia, recurrent airway obstruction (RAO), asthma, chronic obstructive pulmonary disease (COPD), etc.

In a preferred embodiment, the cancer is selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer, and lymphoma.

The invention also provides the water soluble curcumin compound according to the invention for treating proliferative disorders such as neoplasma, dysplasia, premalignant or precancerous lesions, abnormal cell growths, benign tumours, malignant tumours, cancer or metastasis, wherein the cancer is selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer, and lymphoma.

In a preferred embodiment, the patient is a mammal, e.g. a human, horse, rabbit, mouse, rat, pig, sheep, cow or dog. Preferably the subject is a human or a horse.

In preferred pharmaceutical compositions, the water soluble curcumin compound used is the water soluble curcumin compound of general formula I:

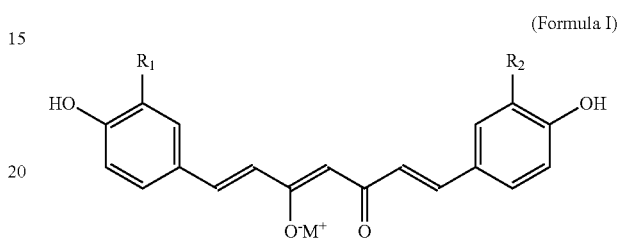

(Formula I)

wherein M is lysine or arginine and R1 and R2 are each independently selected from hydrogen, hydroxy or alkoxy, and/or stereoisomers thereof.

The preferred water soluble curcumin compounds of the invention are cyclodextrin complexes of the compounds of general formula I, and/or stereoisomers thereof.

In an even more preferred embodiment, the curcumin compounds of the invention are hydroxypropyl-beta-cyclodextrin (HP-beta-CD) complexes or hydropropyl-gamma-cyclodextrin (HP-gamma-CD) complexes of the compounds of general formula I.

In the most preferred embodiment, the compound of the invention is a hydroxypropyl-beta-cyclodextrin of curcumin lysinate, called NDS27 or a hydroxypropyl-gamma-cyclodextrin of curcumin lysinate called NDS28.

Curcumin used in the preparation of the water soluble curcumin compound of the invention can be converted, resulting in an acylated derivative or a derivative thereof or a glycosylated derivative.

Alternatively, the water soluble curcumin compound according to the invention can be a cyclodextrin derivative of curcumin, preferably a beta or gamma-cyclodextrin derivative of curcumin, more preferably a gamma-cyclodextrin derivative of curcumin, most preferably HP-gamma-CD-curcumin.

The water soluble curcumin derivative of the invention can be in lyophilised form.

The invention further provides a process for producing a water soluble curcumin compound according to the invention, comprising the following steps:
a) synthesis of pure curcumin using standard methodology
b) synthesis of salts of curcumin lysinate or argininate comprising the steps of:
  (i) dissolving curcumin under heat in methanol (solution 1),
  (ii) dissolving lysine or arginine base in water (solution 2) and
  (iii) stirring solution 2 into solution 1, followed by shaking and evaporation under vacuum,
  (iv) redissolving the non-dissolved residue in ethanol and bringing to boiling point,
  (v) filtering out the non-dissolved residue and placing the ethanol based solution at about −20° C. for about one hour, (vi) collecting the precipitate of curcumin lysinate or argininate, c) preparation of cyclodextrin of curcumin lysinate or argininate comprising the steps of:
(i) providing an aqueous cyclodextrin solution such as HP-beta-CD or HP-gamma-CD
(ii) adding curcumin lysinate or argininate to the cyclodextrin solution in one movement while agitating well
(iii) filtering the resulting solution (d) optionally, the step of esterifying curcumin, resulting in an acylated derivative or a derivative thereof or optionally using a glycosylation step.

In a preferred embodiment of the production process, the cyclodextrin is HP-beta-CD or HP-gamma-CD In a further preferred embodiment, of the production process, the curcumin lysinate is used.

In an alternative embodiment, pure curcumin is used for the derivatisation with cyclodextrin instead of lysinated or argininated curcumin.

The curcumin used for derivatisation can be synthetically manufactured or extracted from its natural sources. Preferably, the more pure synthetic form is used (e.g. C7727 from Sigma).

The invention further provides for a method of treating proliferative and/or inflammatory disorders comprising the step of administering to a patient in need thereof a therapeutically acceptable amount of the soluble curcumin-cyclodextrin composition according to the present invention.

In a preferred embodiment, the curcumin derivative is NDS27 and/or NDS28.

In a further preferred embodiment, the proliferative disorder can be neoplasma, dysplasia, premalignant or precancerous lesions, abnormal cell growths, benign tumours, malignant tumours, cancer or metastasis, wherein the cancer is selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer, or lymphoma, wherein the cancer can be selected from the group of: leukaemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, haematological cancer, and lymphoma.

In a further preferred embodiment, the inflammatory disorder can be any kind of pulmonary inflammation, such as RAO, COPD, asthma, pneumonia and the like.

BRIEF DESCRIPTION OF THE DRAWINGS

FIG. 11: Results of the solubility study of different curcumin-cyclodextrin derivatives.

FIG. 12 shows the solubility of the curcumin-HP-gamma-CD combination.

FIG. 13 shows the effect of different agitation methods used on the solubility of curcumin-cyclodextrin combinations. Clearly the diode array method improves the solubility over the conventional agitating water baths.

FIG. 14 shows the stability of the solubilised curcumin-HP-gamma-CD complex when kept at 25° C. for up to 14 days.

DETAILED DESCRIPTION OF THE PREFERRED EMBODIMENTS

Figure 1:
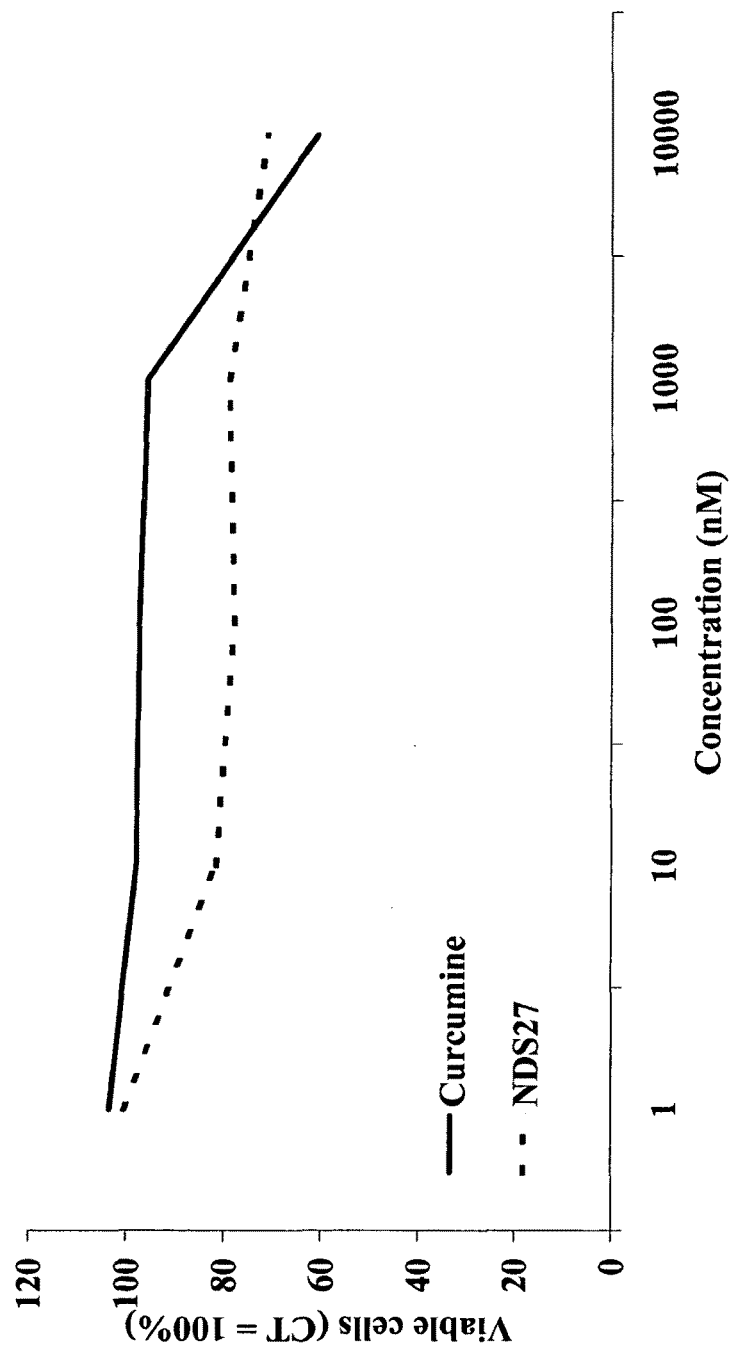
FIG. 1 represents the global growth of different types of tumours as a function of the concentration of curcumin and of the compound according to the invention.

The invention provides new compounds with an anti-cancer and/or anti-inflammatory activity. Said compounds are defined as being cyclodextrin complexes of salts of curcuminoid derivatives of general formula I and any subgroup thereof.

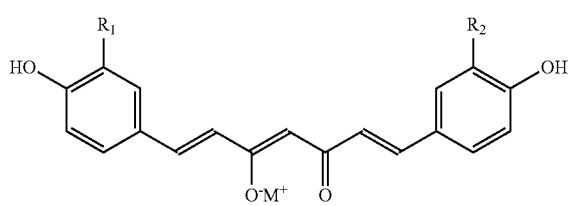

(Formula I)

wherein M is Lysine or Arginine and wherein R1 and R2 are each independently selected from hydrogen, hydroxy or alkoxy In one preferred embodiment, the compound of the invention is a combination of a compound of Formula I with hydroxypropyl-beta-cyclodextrin (HP-beta-CD depicted in Formula II) or with hydroxypropyl-gamma-cyclodextrin (HP-gamma-CD, depicted in Formula III), resulting respectively in a hydroxypropyl-beta-cyclodextrin and hydroxypropyl-gamma-cyclodextrin complex with the compound of Formula I. In the most preferred embodiment, the compound of the invention is a hydroxypropyl-beta-cyclodextrin complex of curcumin lysinate (called NDS27 hereinafter) or the hydroxypropyl-gamma-cyclodextrin complex of curcumin lysinate (called NDS28 hereinafter).

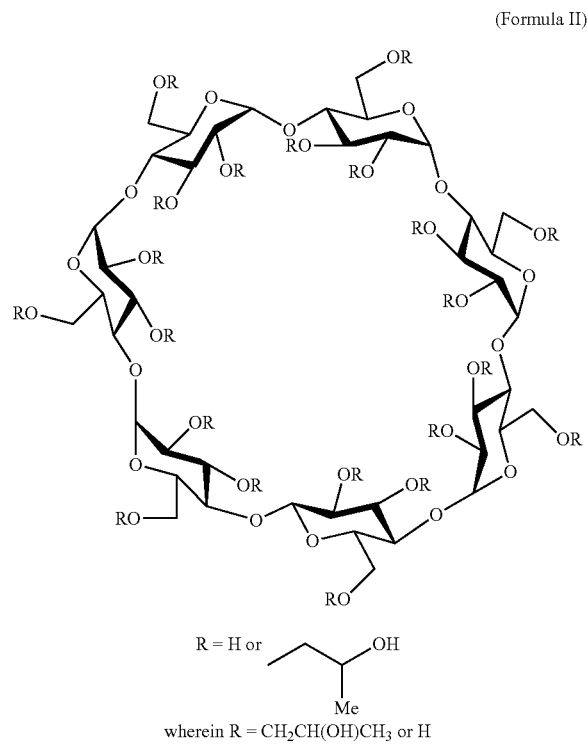

(Formula II)

wherein R = $CH_2CH(OH)CH_3$ or H

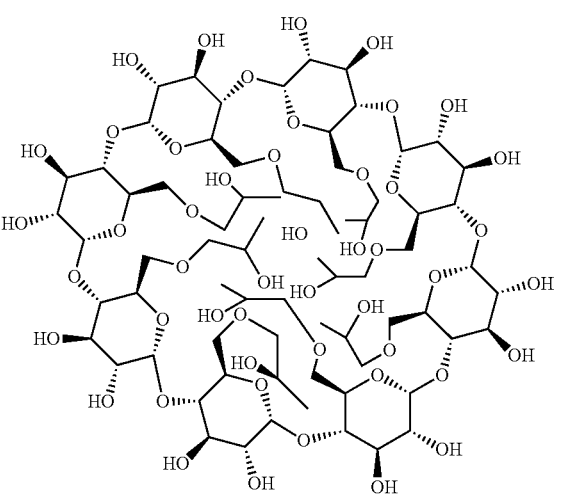

(Formula III)

In an alternative embodiment, the invention provides for alpha-, beta-, and/or gamma-cyclodextrin derivatives of curcumin and their use as anti-proliferative or anti-inflammatory composition. Preferably, said cyclodextrins are hydroxypropyl-cyclodextrins (HP-CD), such as HP-alpha-CD, HP-beta-CD and HP-gamma-CD. Most preferably, the highly soluble and stable HP-beta-CD-curcumin or HP-beta-CD-curcumin-lysinate (NDS27), or the HP-gamma-CD-curcumin or HP-gamma-CD-curcumin-lysinate (NDS28) is used as an anti-proliferative or anti-inflammatory composition. Cyclodextrines are approved FDA drug additives and do not have any known toxic side effects, even when administered in high doses.

Further encompassed by the invention are acylated derivatives of said compounds or compositions or derivatives thereof or a glycosylated derivative of said compounds.

The term "compound(s) of the invention" "compound(s) according to the invention" used throughout the text encompass all curcumin derivatives as mentioned in the above embodiments.

The compounds of the invention have particular advantages since while being anti-proliferative and anti-migratory for cancer cells in vitro, they exhibit a low toxicity level measured in vivo on healthy animals, i.e. rats, mice and ponies. The terms "toxicity" or "toxic effects" as used herein refers to the detrimental effect(s) a compound may have on healthy cells, tissues, or organs. The toxicity level of the compounds according to the invention is surprisingly low. The compounds according to the invention therefore combine the essential features of a good tumour-cell cytotoxic activity and a low level of general toxicity in the treated subject.

In addition, the present invention has established the following advantages of the HP-beta-CD-curcumin and HP-gamma-CD-curcumin compounds of the invention and especially of the NDS27 and NDS28 compounds as defined herein:

Highly water soluble as compared to the naturally occurring curcumin itself, thereby increasing the bioavailability after administration (i.e. concentration of active ingredient curcumin can be significantly increased)

High stability of the curcumin derivatives as shown in the examples below indicating a very good stability for over 7 months when stored at e.g. 4° C. or at −20° C.

A remarkably retained biological activity when administered per os, which is highly unexpected.

Consequently the compounds according to the invention may be used in pharmaceutical compositions for the treatment of various cancers. In addition, because they have a low level of toxicity the compounds according to the invention may be used during longer periods of treatments.

Due to these interesting properties; in particular the anti-proliferative and anti-inflammatory properties and the low level of toxicity, the compounds according to the invention are particularly suitable for use as a medicament, preferably in the treatment of cancer.

Especially for the treatment of lung disorders such as cancers and inflammatory disorders of the lung, the compounds of the invention are very suitable due to their retained activity when orally administered.

In addition, the cyclodextrin derivatives of curcumin and/or its lysine or arginine salt as disclosed by the present invention show unexpected improved solubility and stability characteristics.

Furthermore, the invention provides true experimental data in vitro and in vivo showing the anti-proliferative and anti-inflammatory effect of the improved curcumin compounds of the invention.

Therefore, in another embodiment, the invention relates to compounds according to the invention for use as a medicament. The invention also encompasses the use of at least one compound of the invention, for the preparation of a medicament for treating cancer and/or inflammatory disorders.

In another embodiment, the present invention relates to a pharmaceutical composition comprising a pharmaceutically acceptable excipient and a therapeutic amount of at least one compound according to the invention. The invention also encompasses the use of a pharmaceutical composition comprising a pharmaceutically acceptable excipient and a therapeutic amount of at least one compound according to the invention, for the preparation of a medicament for treating cancer and/or inflammatory disorders.

As indicated above, due to the favourable anti-proliferative and anti-migratory properties on cancer cells and the low level of toxicity, the compounds of the invention are particularly useful in the treatment of individuals suffering from cancer.

The compounds are also particularly useful in the prevention of metastasis as has been established in an in vivo mouse metastasis model.

Accordingly, the present invention provides a method for the treatment of proliferative and/or inflammatory disorders comprising administering to an individual an effective amount of at least one compound of the invention as an active ingredient, such that the proliferative and/or inflammatory disorder is treated. By way of example, in an embodiment of the invention, the proliferative and/or inflammatory disorder is treated in a subject in need of treatment by administering to the subject a therapeutically effective amount of at least one compound of the invention, effective to treat the proliferative and/or inflammatory disorder.

The term "anti-migratory" as used herein refers to the ability of a compound of the invention to stop the migration of cells, required to go away from the neoplastic tumour tissue, and thus to reduce the colonization of new tissues by these cells.

The term "treating" as used herein includes treating any one or more of the conditions underlying or characteristic of a proliferative and/or inflammatory disorder. Treatment of cancer means administration of a medicament with the result that cancer is stabilized reduced or the patient is cured. Treatment of an inflammatory disorder means administration of a medicament with the result that the inflammation is reduced, or the patient is freed from inflammation.

As used herein, the singular forms "a", "an", and "the" include both singular and plural referents unless the context clearly dictates otherwise. By way of example, "an antibody" refers to one or more than one antibody; "an antigen" refers to one or more than one antigen.

The terms "comprising", "comprises" and "comprised of" as used herein are synonymous with "including", "includes" or "containing", "contains", and are inclusive or open-ended and do not exclude additional, non-recited members, elements or method steps.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

All documents cited in the present specification are hereby incorporated by reference in their entirety. In particular, the teachings of all documents herein specifically referred to are incorporated by reference.

The present invention concerns methods and compounds useful for the treatment of proliferative and/or inflammatory disorders.

By "proliferative disease or disorder" is meant all neoplastic cell growth and proliferation, whether malignant or benign, including all transformed cells and tissues and all cancerous cells and tissues. Proliferative diseases or disorders include, but are not limited to, premalignant or precancerous lesions, abnormal cell growths, benign tumours, malignant tumours, and "cancer."

Additional examples of proliferative diseases and/or disorders include, but are not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract. In a preferred embodiment, the proliferative disorder involves tumour.

As used herein, the terms "tumour" or "tumour tissue" refer to an abnormal mass of tissue which results from excessive cell division. A tumour or tumour tissue comprises "tumour cells" which are neoplastic cells with abnormal growth properties and no useful bodily function. Tumours, tumour tissue and tumour cells may be benign or malignant. A tumour or tumour tissue may also comprise "tumour-associated non-tumour cells", e.g., vascular cells which form blood vessels to supply the tumour or tumour tissue. Non-tumour cells may be induced to replicate and develop by tumour cells, for example, the induction of angiogenesis in a tumour or tumour tissue. In another preferred embodiment, the proliferative disorder involves malignancy or cancer.

As used herein, the term "malignancy" refers to a non-benign tumour or a cancer. As used herein, the term "cancer" connotes a type of proliferative disease which includes a malignancy characterized by deregulated or uncontrolled cell growth. Examples of cancer include, but are not limited to, carcinoma, lymphoma, blastoma, sarcoma, and leukaemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, haematological cancer. The term "cancer" includes primary malignant cells or tumours (e.g., those whose cells have not migrated to sites in the subject's body other than the site of the original malignancy or tumour) and secondary malignant cells or tumours (e.g., those arising from metastasis, the migration of malignant cells or tumour cells to secondary sites that are different from the site of the original tumour).

Preferably, said cancer is selected from non-small cell lung cancer, CNS cancer, melanoma, ovarian cancer, kidney cancer, prostate cancer, breast cancer, colon cancer, bladder cancer, sarcoma, pancreatic cancer, colorectal cancer, head and neck cancer, liver cancer, stomach cancer, oesophageal cancer, or lymphoma.

Most preferably, said cancer is selected from colon cancer; prostate cancer; breast cancer; head and neck cancer; glioma, preferably glioblastoma or non-small-cell lung cancer (NSCLC).

Other examples of cancers or malignancies include, but are not limited to: Acute Childhood Lymphoblastic Leukaemia, Acute Lymphoblastic Leukaemia, Acute Lymphocytic Leukaemia, Acute Myeloid Leukaemia, Adrenocortical Carcinoma, Adult (Primary) Hepatocellular Cancer, Adult (Primary) Liver Cancer, Adult Acute Lymphocytic Leukaemia, Adult Acute Myeloid Leukaemia, Adult Hodgkin's Disease, Adult Hodgkin's Lymphoma, Adult Lymphocytic Leukaemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukaemia, Childhood Acute Myeloid Leukaemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukaemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukaemia, Chronic Myelogenous Leukaemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukaemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukaemia, Myeloid Leukaemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumour, and any other proliferative disease, besides neoplasia, located in an organ system listed above.

In a further embodiment, the proliferative disorder is premalignant condition. Premalignant conditions are known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell 1976 (Basic Pathology, 2d Ed., W. B. Saunders Co., Philadelphia, pp. 68-79).

"Hyperplasia" is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

"Metaplasia" is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

"Dysplasia" is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia. epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders include, but are not limited to, benign dysproliferative disorders (e.g., benign tumours, fibrocystic conditions, tissue hypertrophy, intestinal polyps, colon polyps, and oesophageal dysplasia), leukoplakia, keratoses, Bowen's disease, Farmer's Skin, solar cheilitis, and solar keratosis.

In preferred embodiments, the proliferative disorder is chosen from glioma, preferably glioblastoma; prostate cancer; lung cancer, non-small-cell lung cancer (NSCLC); or colon cancer. The inventors realised that the above cancer types can particularly benefit from the methods and agents of the invention.

As used herein, the term "glioma" refers to its art-recognised connotation. By virtue of further illustration and not limitation, the term "glioma" refers to a tumour originating in the neuroglia of the brain or spinal cord. Gliomas can be derived from glial cell types, such as, e.g., astrocytes and oligodendrocytes, thus gliomas include astrocytomas and oligodendrogliomas, as well as anaplastic gliomas, glioblastomas, and ependymonas. Astrocytomas and ependymomas can occur in all areas of the brain and spinal cord in both children and adults. Oligodendrogliomas typically occur in the cerebral hemispheres of adults. Malignant astrocytic gliomas are associated with the worst prognoses because of their ability to infiltrate diffusely into the normal brain parenchyma and include World Health Organization (WHO) grades II, III and grade IV tumours.

As used herein, the term "glioblastoma" refers to its art-recognised connotation. By virtue of further illustration and not limitation, glioblastoma may also be known as "glioblastoma multiforme" (GBM) or as "grade 4 astrocytoma" and represents perhaps the most common and aggressive type of malignant primary brain tumour.

As used herein, the term "prostate cancer" (CaP) refers to its art-recognised connotation. By virtue of illustration and not limitation, the term "prostate cancer" refers to both the appearance of a palpable tumour of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Cancer cells are generally found in the prostates of men who live into their seventies or eighties, however not all of these men develop prostate cancer. In the event that prostate cancer metastasises to additional sites distal to the prostate, the condition is described as metastatic cancer (MC), to distinguish this condition from organ-confined prostate cancer. CaP fatality typically results from metastatic dissemination of prostatic adenocarcinoma cells to distant sites, usually in the axial skeleton.

The term "non-small-cell lung cancer" (NSCLC) refers to its art-recognised connotation. By means of exemplification and not limitation, the term encompasses any of subtypes thereof, i.e., adenocarcinoma of the lung, squamous cell carcinoma of the lung and large cell carcinoma of the lung.

The term "colon cancer" refers to its art-recognised connotation. By means of illustration and not limitation, the term "colon cancer" refers to cancers arising in the large intestine (including both the colon and rectum) of any histologic type, including but not limited to malignant epithelial tumours. As used herein the term colon cancer thus encompasses colorectal cancer. Malignant epithelial tumours of the large intestine may be divided into five major histologic types: adenocarcinoma, mucinous adenocarcinoma (also termed colloid adenocarcinoma), signet ring adenocarcinoma, scirrhous tumours and carcinoma simplex. Colon cancer is staged using any of several classification systems known in the art. The Dukes system is one of the most often employed staging systems. See Dukes and Bussey 1958 (Br J Cancer 12: 309).

Clinical data indicates that patients displaying pulmonary inflammatory diseases develop more often lung tumours. These data suggest that a persistent pulmonary inflammation might alter the organ's properties to develop tumours but the exact mechanisms connecting chronic inflammatory processes to cancer are not yet well known. Our findings suggest that curcumin might be a candidate for a combined therapy against lung cancer.

In a preferred embodiment of the present invention, the cancer to be treated by the water soluble curcumin compound is therefore lung cancer.

The present invention also provides methods of treating proliferative and/or inflammatory disorders in a subject needing such therapy, comprising administering a therapeutically effective amount of the compounds of the invention.

The present invention also provides methods of treating oxidative and inflammatory disorders in a subject needing such therapy, comprising administering a therapeutically effective amount of the compounds of the invention.

The "inflammatory disorder" can be, for example, rheumatoid arthritis, psoriasis, ulcerative colitis, inflammatory diseases of gastro-intestinal tract such as Crohn's disease and adenomatous polyposis, central nervous system diseases, preferably Alzheimer's disease, neuropathies and stroke, atherosclerosis, diabetes, arthritis and graft-versus host diseases such as transplant rejection, ankylosing spondylitis, fibromyalgia, asthma, chronic obstructive pulmonary disease (COPD), multiple sclerosis, type I diabetes, systemic lupus erythematosus, scleroderma, systemic sclerosis, Sjögren's syndrome, autoimmune disorders, chronic inflammation, allergic reactions and hypersensitivities, inflammatory bowel diseases, reperfusion injury, rheumatoid arthritis and the like. In a preferred embodiment, the inflammatory disorder is a lung inflammatory disorder such as pneumonia, bronchitis, recurrent airway obstruction (RAO) etc.

Except when noted, "subject" or "patient" are used interchangeably and refer to animals, preferably vertebrates, more preferably mammals, and specifically includes human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Accordingly, "subject" or "patient" as used herein means any mammalian patient or subject to which the compositions of the invention can be administered. Preferred patients are horses and human subjects.

As used herein, the terms "treat" or "treatment" refer to both therapeutic treatment and prophylactic or preventative measures, wherein the object is to prevent or slow down (lessen) an undesired physiological change or disorder, such as the development or spread of proliferative disease, e.g., cancer or development and persistence of inflammation. Beneficial or desired clinical results include, but are not limited to, alleviation of symptoms, diminishment of extent of disease, stabilised (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a phrase such as "a subject in need of treatment" includes subjects, such as mammalian subjects, that would benefit from treatment of a given condition, preferably a proliferative disease, such as, e.g., cancer or an inflammatory disorder such as e.g. RAO as above.

Such subjects will typically include, without limitation, those that have been diagnosed with the condition, preferably a proliferative and/or inflammatory disease, e.g., cancer, those prone to have or develop the said condition and/or those in whom the condition is to be prevented.

The term "therapeutically effective amount" refers to an amount of a therapeutic substance or composition effective to treat a disease or disorder in a subject, i.e., to obtain a desired local or systemic effect and performance. By means of example and not limitation, in the case of proliferative disease, e.g., cancer, therapeutically effective amount of a drug may reduce the number of cancer cells; reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; enhance efficacy of another cancer therapy; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). The term thus refers to the quantity of compound or pharmaceutical composition that elicits the biological or medicinal response in a tissue, system, animal, or human that is being sought by a researcher, veterinarian, medical doctor or other clinician, which includes alleviation of the symptoms of the cancer being treated. In particular, these terms refer to the quantity of compound or pharmaceutical composition according to the invention which is necessary to prevent, cure, ameliorate, or at least minimize the clinical impairment, symptoms, or complications associated with cancer in either a single or multiple doses.

For use in inflammatory disorders, treatment refers to reducing or stabilizing inflammation and eventually freeing the subject under treatment form inflammation.

The compounds of the invention may be used alone or in combination with any of the cancer therapies selected from the group comprising chemotherapy, radiation therapy, immunotherapy, and/or gene therapy. As used herein the term "cancer therapy" is meant to encompass radiation therapy, chemotherapy, immunotherapy, gene-based therapy, surgery, as well as combinations thereof.

In another preferred embodiment the compounds of the invention may be used alone or in combination with one or more active compounds that are suitable in the treatment of cancer, preferably glioma, preferably glioblastoma; prostate cancer; NSCLC; or colon cancer. The term "active compound" refers to a compound other than the agents of the invention which is used to treat cancer. The active compounds may preferably be selected from the group comprising radiation therapeutics, chemotherapeutics including but not limited to temozolomide, vincristine, vinorelbine, procarbazine, carmustine, lomustine, taxol, taxotere, tamoxifen, retinoic acid, 5-fluorouracil, cyclophosphamide and thalidomide, immunotherapeutics such as but not limited to activated T cells and pulsed dendritic cells, and/or gene-based therapeutic approached involving gene transfer of CD3, CD7 and CD45 in glioma cells, concomitantly with the delivery of the agents of the invention.

Alternatively, the compounds of the invention can be administered in combination with adjuvants able to increase or regulate humoral and/or cellular response of the immune system against the active principle or against the vehicle or carrier so as to reduce or suppress side-effects or toxic effects associated to the active principle and/or the vehicle or carrier. An example refers to the use of anti-galectin-1 agents because galectin-1, which is a small protein secreted by cancer cells, kills activated T cells that attack cancer cells.

The compounds of the invention can thus be administered alone or in combination with one or more active compounds, e.g. other anti-cancer or anti-inflammatory compounds. The latter can be administered before, after or simultaneously with the administration of the said agent(s).

A further object of the invention are pharmaceutical preparations which comprise a therapeutically effective amount of the compounds of the invention as defined herein, or pharmaceutically acceptable salts thereof, and a pharmaceutically acceptable carrier, i.e., one or more pharmaceutically acceptable carrier substances and/or additives, e.g., buffers, carriers, excipients, stabilisers, etc.

The term "pharmaceutically acceptable" as used herein is consistent with the art and means compatible with the other ingredients of a pharmaceutical composition and not deleterious to the recipient thereof.

The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

The pharmaceutical composition according to the invention may further comprise at least one active compound, as defined above.

The pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. Preferred modes of administration are per os (i.e. oral) administration and/or inhalation and intravenous administration.

The pharmaceutical composition can be prepared in a manner known per se to one of skill in the art. For this purpose, at least one compound having Formula I or a cyclodextrin complex thereof as defined above, one or more solid or liquid pharmaceutical excipients and, if desired, in combination with other pharmaceutical active compounds, are brought into a suitable administration form or dosage form which can then be used as a pharmaceutical in human medicine or veterinary medicine.

By means of non-limiting examples, such a formulation may be in a form suitable for oral administration, for parenteral administration (such as by intravenous, intramuscular, or subcutaneous injection, or intravenous infusion), for topical administration (including ocular), for administration by inhalation, by a skin patch, by an implant, by a suppository, etc. Such suitable administration forms—which may be solid, semi-solid, or liquid, depending on the manner of administration—as well as methods and carriers, diluents and excipients for use in the preparation thereof, will be clear to the skilled person; reference is made to for instance U.S. Pat. No. 6,372,778, U.S. Pat. No. 6,369,086, U.S. Pat. No. 6,369,087, and U.S. Pat. No. 6,372,733, as well as to the standard handbooks, such as the latest edition of Remington's Pharmaceutical Sciences.

It has furthermore been shown in the present invention that the soluble curcumin compound as disclosed herein is particularly miscible with 1% hyaluronic acid, which makes it possible to administer the compound by peritoneal irrigation.

Preferably, the present composition is administered in a GLP/GMP solvent, or hyaluronic acid solvent containing or not hydroxypropyl-beta-cyclodextrin, hydroxypropyl-gamma-cyclodextrin and/or similar compounds.

For treating animals (e.g. horses), the soluble curcumin compound of the present invention can be administered using intra-articular injection.

As non-limiting examples, the active compound, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human medicine. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the nucleic acid and/or the active compound and to use the resulting lyophilisates, for example, for preparing preparations for injection or infusion. Suitable carriers for microcapsules, implants or rods are, for example, copolymers of glycolic acid and lactic acid.

The pharmaceutical preparations can also contain additives, for example fillers, desintegrants, binders, lubricants, wetting agents, stabilizers, emulsifiers, dispersants, preservatives, sweeteners, colorants, flavourings, aromatizers, thickeners, diluents, buffer substances, solvents, solubilisers, agents for achieving a depot effect, salts for altering the osmotic pressure, coating agents or antioxidants.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate, and lactose and/or other excipients, binders, extenders, disintegrants, diluents, and lubricants known in the art.

The oral administration of a pharmaceutical composition comprising at least one compound according to the invention, or a pharmaceutically acceptable salt or ester and/or solvate thereof, is suitably accomplished by uniformly and intimately blending together a suitable amount of said compound in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Some preferred, but non-limiting examples of such preparations include tablets, pills, powders, lozenges, sachets, cachets, elixirs, suspensions, emulsions, solutions, syrups, aerosols, ointments, crèmes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying, and suspending agents, dispersing agents, desintegrants, bulking agents, fillers, preserving agents, sweetening agents, flavouring agents, flow regulators, release agents, etc. The compositions may also be formulated so as to provide rapid, sustained, or delayed release of the active compound(s) contained therein, for example using liposomes or hydrophilic polymeric matrices based on natural gels or synthetic polymers.

The dosage or amount of compounds of the invention used, optionally in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. A preferred dosage of the agent may be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks.

The pharmaceutical preparations of the invention are preferably in a unit dosage form, and may be suitably packaged, for example in a box, blister, vial, bottle, sachet, ampoule, or in any other suitable single-dose or multi-dose holder or container (which may be properly labelled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300, or 400 mg per unit dosage. Preferably the dose is 60 mg/kg/day in mice, corresponding to ~5 mg/kg in humans, i.e. 300 mg per dose.

By way of example, the agents of the invention may be delivered at the site of the tumour, e.g., the primary tumour and/or metastases or to the site of inflammation e.g. the lungs by inhalation. A manner of achieving localized delivery is the use of the Ommaya reservoir as described elsewhere.

In another embodiment, the invention provides a kit comprising a pharmaceutical composition according to the invention, and an active compound as defined herein, for simultaneous, separate or sequential administration to a subject in need thereof.

For these purposes, the compounds or the pharmaceutical compositions of the present invention may be administered orally, parenterally, i.e. including subcutaneous injections, intravenous, intramuscular, intra-sternal injection, or infusion techniques, by inhalation, inhalation spray, or rectally, in dosage unit formulations containing conventional non-toxic pharmaceutically acceptable carriers, adjuvants, and vehicles. At least one compound of the invention will generally be administered in an "effective amount", by which is meant any amount of a compound of the Formula I or a cyclodextrin salt thereof as defined above that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight, more often between 0.1 and 500 mg, such as between 1 and 250 mg, for example about 5, 10, 20, 50, 100, 150, 200, or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

Essentially, the primary modes of treatment of solid tumour cancers comprise surgery, radiation therapy, and chemotherapy, separately and in combination. The compounds according to the invention are suitable for use in combination with these medicinal techniques. The compounds of the invention may be useful in increasing the sensitivity of tumour cells to radiation in radiotherapy and also in potentiating or enhancing damage to tumours by chemotherapeutic agents. The compounds and their pharmaceutically acceptable salts and/or solvates may also be useful for sensitizing multidrug-resistant tumour cells. The compounds according to the invention are useful therapeutic compounds for administration in conjunction with DNA-damaging cytotoxic drugs or radiation used in radiotherapy to potentiate their effect.

In another embodiment of the method of the invention, the administration may be performed with food, e.g., a high-fat meal. The term "with food" means the consumption of a meal either during or no more than about one hour before or after administration of a pharmaceutical composition according to the invention.

Oral administration of a pharmaceutical composition comprising at least one compound according to the invention, or a pharmaceutically acceptable salt or ester and/or solvate thereof can also be accomplished by preparing capsules or tablets containing the desired amount of said compound, optionally blended with a solid carrier as described above. Compressed tablets containing the pharmaceutical composition of the invention can be prepared by uniformly and intimately mixing the active ingredient with a solid carrier such as described above to provide a mixture having the necessary compression properties, and then compacting the mixture in a suitable machine to the shape and size desired. Moulded tablets maybe made by moulding in a suitable machine, a mixture of powdered compound moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions, or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound of the invention, if desired with the substances customary therefore such as solubilisers, emulsifiers, or further auxiliaries, are brought into solution, suspension, or emulsion. The compounds of the invention can also be lyophilized and the lyophilizates obtained used, for example, for the production of injection or infusion preparations. Suitable solvents are, for example, water, physiological saline solution, or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents, or solvents, such as mannitol, 1,3-butanediol, water, Ringer's solution, or isotonic sodium chloride solution, or suitable dispersing or wetting and suspending agents, such as sterile, bland, fixed oils, including synthetic mono- or diglycerides, and fatty acids, including oleic acid. When rectally administered in the form of suppositories, these formulations may be prepared by mixing the compounds according to the invention with a suitable non-irritating excipient, such as cocoa butter, synthetic glyceride esters, or polyethylene glycols, which are solid at ordinary temperatures, but liquidify and/or dissolve in the rectal cavity to release the drug.

The pharmaceutical compositions of this invention can be administered to humans or animals in dosage ranges specific for each compound comprised in said compositions. The compounds comprised in said composition can be administered together or separately.

It will be understood, however, that specific dose level and frequency of dosage for any particular patient or animal subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Curcumin has been shown to exhibit a great therapeutic potential in various chronic diseases, in which inflammation plays a major role, and has particularly interesting anti-inflammatory and antioxidant properties. These diseases include Alzheimer's disease Parkinson's disease, multiple sclerosis, epilepsy, cerebral injury, cardio vascular diseases, cancer, allergy, asthma, bronchitis, colitis, rheumatoid arthritis, degenerative joint disease, renal ischemia, psoriasis, diabetes, obesity, depression, fatigue, and AIDS (Aggarwal, The International Journal of Biochemistry & Cell Biology 41(2009)40-59).

In horses, inflammatory diseases are extremely frequent. Excessive activation and degranulation of neutrophiles occur in several conditions, such as endotoxinic shock, laminitis, peritonitis, arthritis, recurrent airway obstruction.

Curcumin reduces inflammation through multiple pathways:

Decreasing the monocytes and neutrophiles activation

Decreasing the reactive oxygen species generated by the activated neutrophiles

Decreasing the release of proteasic and oxidative enzymes by the activated neutrophiles and in particular, the release and the activity of myeloperoxidase downregulating the expression of interleukin (IL)-6 protein, TNF, and various other chemokines inhibiting the production of IL-8, MIP-1a, MCP-1, IL-1b, and TNF-a induced by inflammatory stimuli in human peripheral blood monocytes and alveolar macrophages downregulating the expression of the NF-kB-regulated gene products such as COX-2, TNF, 5-LOX, IL-1, IL-6, IL-8, MIP-1a, adhesion molecules, c-reactive protein (CRP), CXCR-4, and others binding to COX-2 and 5-LOX and to inhibit their activity binding to IkBa kinase needed for NF-kB activation inhibiting STAT 3, another transcription factor through which proinflammatory cytokine IL-6 mediates its effects Below, some examples of preferred embodiments of uses of the curcumin composition of the present invention are listed. These are however not to be seen as limiting the scope of the invention.

Human and Equine Inflammatory Respiratory Diseases

In human patients with severe asthma or chronic obstructive pulmonary disease (COPD), an inflammatory condition exists that leads to activation of the NF-kB pathway. A change also occurs in the histone acetylation and deacetylation balance via posttranslational modification of histone deacetylases (HDACs). HDAC2 plays a major role in insensitivity to corticosteroid treatment in asthma and COPD. It has been shown that curcumin can restore HDAC activity, thereby restoring corticosteroid function.

Equine recurrent airway obstruction (RAO) is a naturally occurring respiratory disease in horses with many similarities to human asthma and, as a result, has been used as an animal model of this disease. Oxidative stress has been demonstrated to occur in a range of respiratory diseases in horse and in human beings including asthma and has been attributed also to the neutrophiles activation.

The present invention shows a clear effect of the soluble curcumin compound of the invention in ameliorating the inflammatory condition of the airways when inhaled.

Human and Equine Inflammatory Joint Diseases

Osteoarthritis (OA) results from articular cartilage failure induced by a combination of genetic, metabolic, biochemical, and biomechanical factors. OA is normally treated with analgesics such as acetaminophen and opioids, NSAIDs, and intra-articular therapies such as glucocorticoids and hyaluronans.

In human patients, rheumatoid arthritis (RA) is a chronic inflammatory disease that is characterized by hyperplasia of the synovial fibroblasts, which is in part the result of decreased apoptosis. Clinically, the disease appears as joint stiffness and swelling, often manifesting in a symmetrical pattern on both sides of the body. The roles of inflammatory cytokines, such as TNF, IL-1, IL-6, and chemokines; inflammatory enzymes such as COX-2, 5-LOX, and MMP-9; and adhesion molecules in the pathogenesis of arthritis are well documented. Almost all the inflammation mediators linked to arthritis have been shown to be regulated by the transcription factor NF-kB. Curcumin downregulates the expression of the NF-kB-regulated gene products.

On several culture models of chondrocytes and synoviocytes, curcumin has produced beneficial effects. Matrix metalloproteinases (MMPs) are responsible for the pathologic features and cause the degradation of cartilage. It was shown that mRNA upregulation of MMPs was inhibited by curcumin.

The present invention further provides for the use of the soluble curcumin compound of the invention in treating inflammatory joint diseases means of intra-articular injection.

Human and Equine Peritonitis and Peritoneal Adhesions

Post surgical adhesions are common complications after abdominal surgery in human and equine patients. Intra-abdominal adhesions occurring in the postoperative period are among the most important causes of chronic abdominal pain and intestinal obstruction after laparotomy. The key molecules implicated in the adhesion formation are the growth factors, cytokines, chemokines, proteases and extracellular matrix that are recognized to regulate inflammation, fibrinolysis, angiogenesis, and tissue remodelling. Curcumin could also reduce the incidence of these post-surgical adhesions.

The present invention further provides for the use of the water soluble curcumin compound of the invention in treating peritonitis and peritoneal adhesions by means of peritoneal irrigation. Preferably, said composition is mixed with hyaluronic acid.

EXAMPLES

The invention is illustrated by the following non-limiting examples. Although the studies below were performed using either one of the compositions HP-beta-CD-curcumin, NDS27 or NDS28, we do believe that all compositions according to the invention are interchangeably usable for the uses shown in all the examples.

This is particularly exemplified by the anti-cancer effect of both the HP-gamma-CD-curcumin and HP-beta-CD-curcumin-lysinate (NDS27). The only major difference between the different compositions according to the invention is their water solubility. The NDS28 composition for example is more water soluble than the NDS27 composition, suggesting that this compound may yet have even better anti-cancer and/or anti-proliferative properties than the NDS27 composition due to its increased bio-availability e.g. through per os administration. Further experiments showing the effect of different compounds according to the invention are ongoing.

Example 1

HPLC Dosages of Curcumin, Curcumin Lysinate and NDS27

All methods described to date had the major disadvantage of over-estimating the concentrations of curcumin in plasma because in all these analytical conditions, curcumin showed exactly the same retention times as bilirubin. This induced thus recovery from the integration surfaces and quantifying errors.

For the new method that was developed, the mobile phase is composed of THF/citrate buffer brought to a pH of 6 with KOH. For its preparation, 10 g of citric acid were dissolved in one liter of water for HPLC. The pH was adjusted to 6 with KOH for HPLC. 666 ml of THF for HPLC were added. It was then homogenised and filtered on HPLC 22µ filters. Gas was expelled with ultrasound. The detection wavelength used is 429 nm and the flow rate is 0.7 ml/minute. The stationary phase is Lichrospher column C18, 125 mm, 5µ.

Using this new method, retention time of curcumin, curcumin lysinate and NDS27 is 8.34 minutes, retention time of demethoxycurcumin is 9.56 minutes, retention time of bis-demethoxycurcumin is 10.93 minutes and the retention time of bilirubin is different than the retention time of curcumin, Curcumin Lysinate and NDS27 i.e. 6.24 minutes.

Apparatus:
Merck Hitachi L-4000 UV Detector
Merck Hitachi L-6000 Pump
Merck Hitachi D-2000 Chromato-Integrator

Example 2

Synthesis of the Compound According to the Invention

A/ Synthesis of Curcumin at Ambient Temperature in Ethyl Acetate.

Curcumin was synthesised according to the method described by H. J. J. Pabon (Recueil, 83, 379-386, 1964).

60 g of vanillin (0.4 mole) and 210 ml (184 g) of tributyl borate (0.8 mole) were rendered soluble in 200 ml of anhydrous ethyl acetate. The product formed by the reaction of 20 g of acetylacetone (0.2 mole) and of 10 g of boric anhydride (0.14 mole) was then added while stirring. After 5 minutes, while still stirring, 1 ml of butylamine was added every 10 minutes (total: 4 ml). The agitation was continued for another 4 hours, then the reaction was set aside overnight. The following day, 300 ml of concentrated hydrochloric acid were added. Agitation was continued for one hour. The phases were then separated and the aqueous phase was extracted three times with 100 ml of ethyl acetate. The solutions of ethyl acetate were gathered and washed in turn with 150 ml of diluted hydrochloric acid. The ethyl acetate solution was then concentrated in vacuum until a final volume of around 150 ml was obtained.

Methanol was then added, and after three hours in the refrigerator, curcumin was collected by filtration and dried.

In contrast with the commercially available extract of turmeric which is erroneously presented as pure curcumin, we actually obtained the desired compound.

This synthesis offers the advantage of being reproducible, reliable, and can be transposed with satisfying output to industrial production to provide a product well adapted to pharmaceutical requirements.

Yield: 68% of crystals of a red-orange colour.
Melting point ("m.p."): 176-178° C.
From the parent solution, a second quantity of crystals of 3 g of curcumin was obtained the following day by filtration.
m.p: 176-178° C.
Yield: 73%
RF of curcumin on TLC aluminium plates with silicium gel 60F-254 for a mobile choloroform-methanol phase (9.25: 0.75 v/v) is 0.48.

B/ Synthesis of the Curcumin Lysinate Salt

Curcumin: $C_{21}H_{20}O_6$: MM: 368.3854: Yellow powder.
Lysine Base: $C_6H_{14}N_2O_2$ MM: 146.19: White powder.
Curcumin Lysinate: $C_{27}H_{34}N_2O_8$ MM: 514.5754: Dark red crystalline powder.

For one part, 500 mg of curcumin were dissolved under heat, (0.00136M) in 50 ml of methanol (Solution 1). For the other part, 198.4 mg of lysine base (0.00136M) were dissolved in 5 ml of water (solution 2). While stirring, solution 2 was added into solution 1 and the mixture was shaken for 5 minutes and then evaporated under vacuum. The non-dissolved residue was taken back with 50 ml of ethanol and was brought to boiling point. The non-dissolved residue was then filtered out. The ethanol based solution was placed at −20° C. for one hour. The precipitate of curcumin lysinate was then collected by filtration.

Yield: 90%.

Elementary Analysis of curcumin lysinate salt: CHN
Apparatus: Thermo Interscience Flash EA 1112 Series
C: 63.02%
H: 6.66%
N: 5.44%

Results of Analysis
C: 63.12%
H: 6.62%
N: 5.49%

Figure 4:
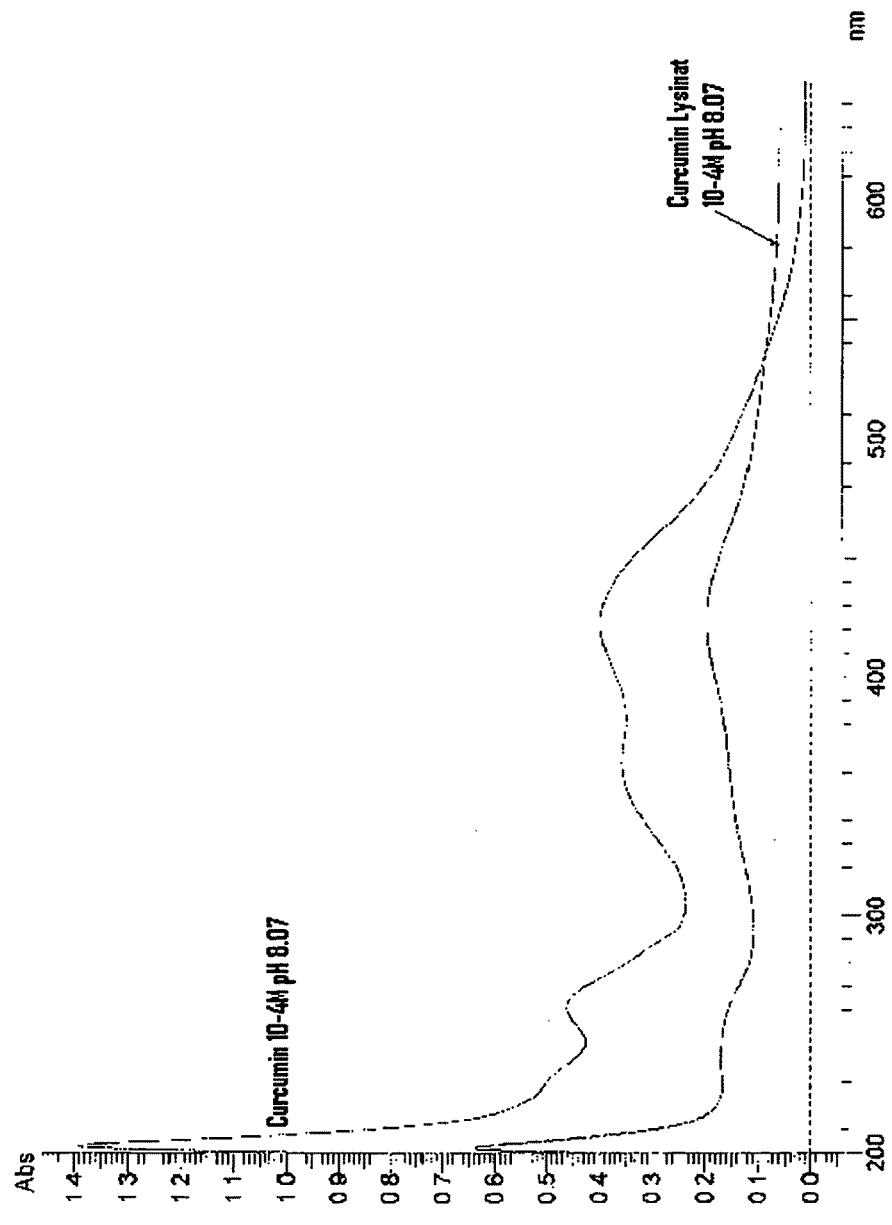
FIG. 4 represents the UV-spectrometric analysis of curcumin and curcumin lysinate.

UV Spectrometry Analysis:

Apparatus: UV: Hitachi U-3010 Spectrophotometer, results see FIG. 4 for both pure curcumin and curcumin lysinate and the data sets below.

Pure Curcumin:

| | |
|---|---|
| Sample: | curc10-4M pH 8.07 |
| Run Date: | 13:29:46, Jun. 03, 2003 |
| Operator: | LCP |
| Instrument: | |
| Model: | U-3310 Spectrophotometer |
| ROM version: | 2520 10 |

Instrument Parameters

| | |
|---|---|
| Measurement type: | Wavelength scan |
| Data Mode: | Abs |
| Starting Wavelength: | 650.00 nm |
| Ending Wavelength: | 200.00 nm |
| Scan speed: | 120 nm/min |
| Sampling Interval: | 0.20 nm |
| Slit Width: | 1 nm |
| PMT Voltage: | Auto |
| Lamp Change: | 340.00 nm |
| Baseline Correction: | System |
| Smoothing: | Off |
| Path Length: | 10.0 nm |

Peak Integration

| | |
|---|---|
| Method: | Rectangular |
| Sensitivity: | 1 |
| Threshold: | 0.0100 |

Peaks

| Peak # | Start | Apex (nm) | End (nm) | Height (Abs) | Area (Abs nm) | Valley (nm) |
|---|---|---|---|---|---|---|
| 1 | 650.00 | 421.00 | 292.60 | 0.198 | 42.743 | 292.60 |
| 2 | 292.60 | 202.20 | 200.00 | 0.638 | 17.740 | 200.00 |

Curcumin Lysinate:

| | |
|---|---|
| Sample: | curclys10-4M pH 8.07 |
| Run Date: | 14:33:12, Jun. 03, 2003 |
| Operator: | LCP |
| Instrument: | |
| Model: | U-3310 Spectrophotometer |
| ROM version: | 2520 10 |

Instrument Parameters

| | |
|---|---|
| Measurement type: | Wavelength scan |
| Data Mode: | Abs |
| Starting Wavelength: | 650.00 nm |
| Ending Wavelength: | 200.00 nm |
| Scan speed: | 120 nm/min |
| Sampling Interval: | 0.20 nm |
| Slit Width: | 1 nm |
| PMT Voltage: | Auto |
| Lamp Change: | 340.00 nm |
| Baseline Correction: | System |

| | |
|---|---|
| Smoothing: | Off |
| Path Length: | 10.0 nm |
| Peak Integration | |
| Method: | Rectangular |
| Sensitivity: | 1 |
| Threshold: | 0.0100 |

| Peaks | | | | | | |
|---|---|---|---|---|---|---|
| Peak # | Start | Apex (nm) | End (nm) | Height (Abs) | Area (Abs nm) | Valley (nm) |
| 1 | 650.00 | 420.80 | 307.20 | 0.400 | 68.271 | 307.20 |
| 2 | 307.20 | 261.00 | 246.80 | 0.463 | 21.723 | 246.80 |
| 3 | 246.80 | 203.20 | 200.00 | 1.391 | 30.872 | 200.00 |

Figure 5:
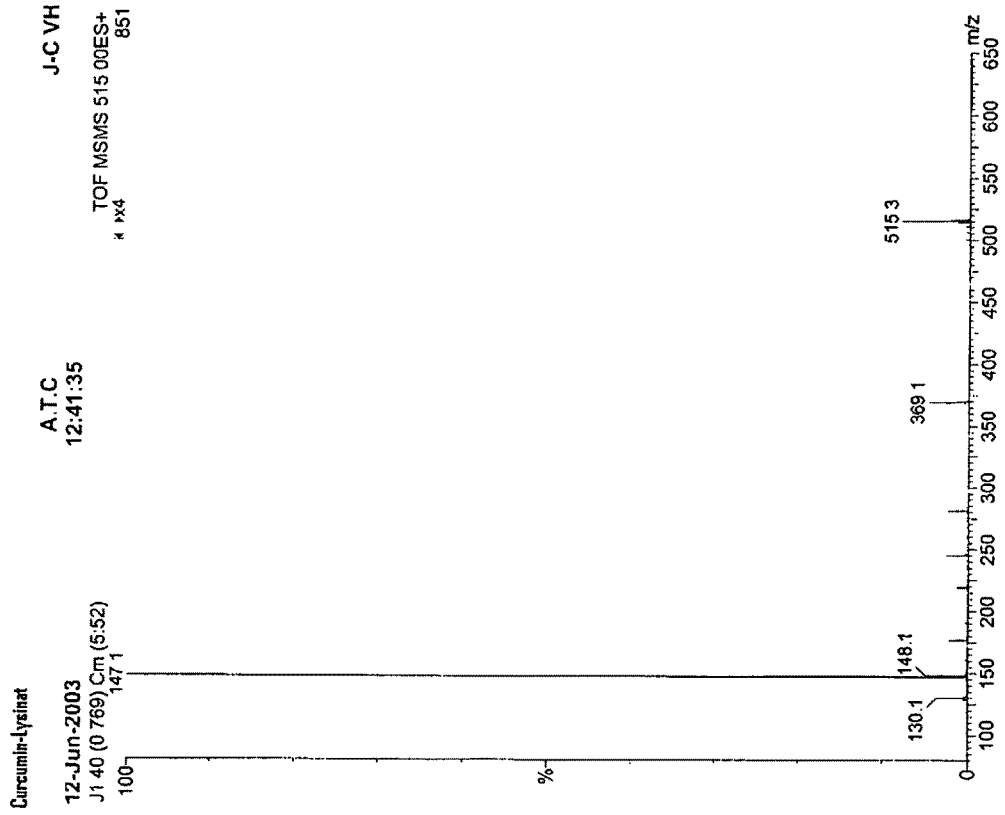
FIG. 5 represents a graph of the mass spectroscopic analysis of the curcumin lysinate composition of the invention.

Mass spectrometry analysis: For results see FIG. 5

Figure 6:
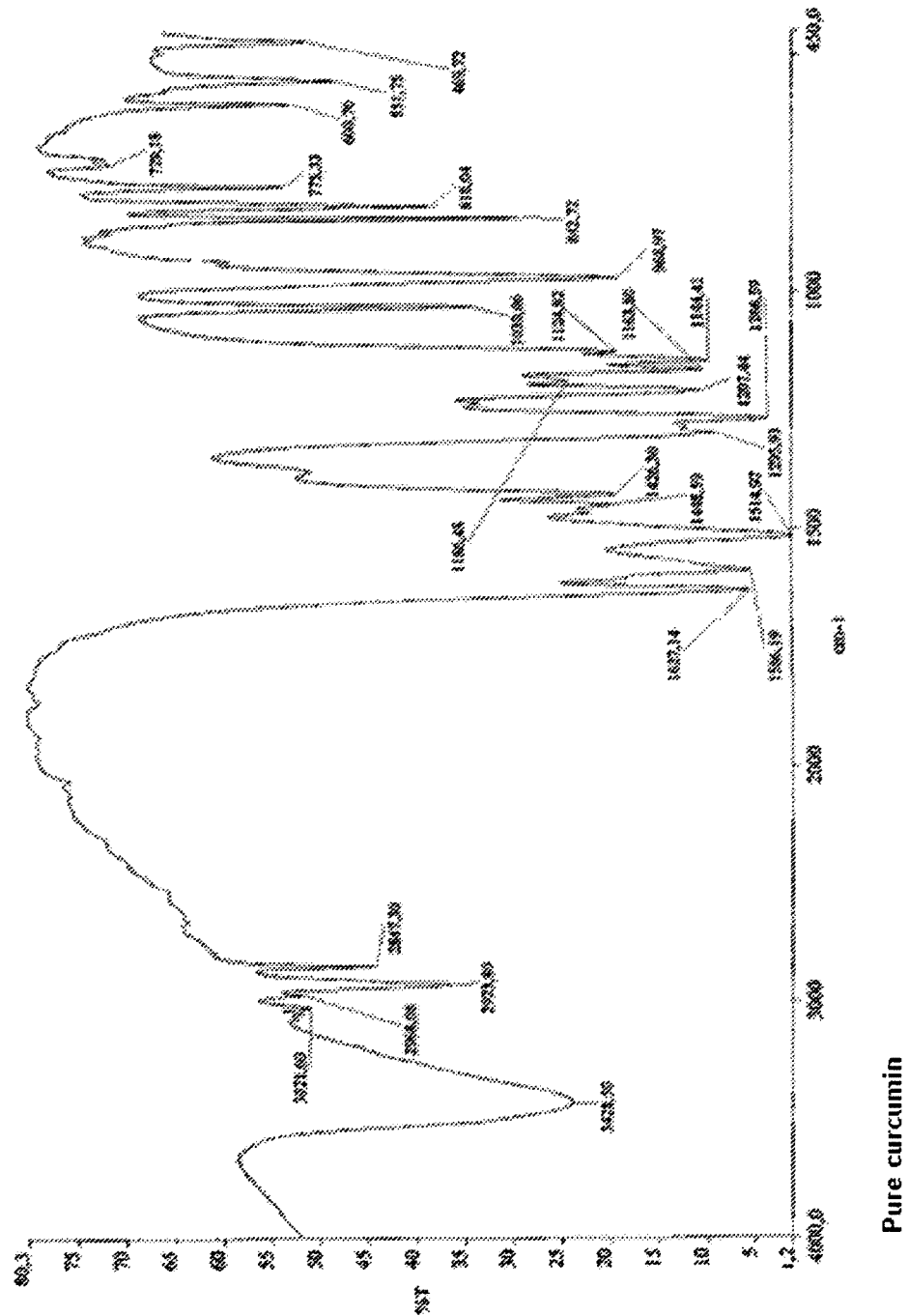
FIG. 6 represents a graph of the FTIR analysis of the pure curcumin composition.
Figure 7:
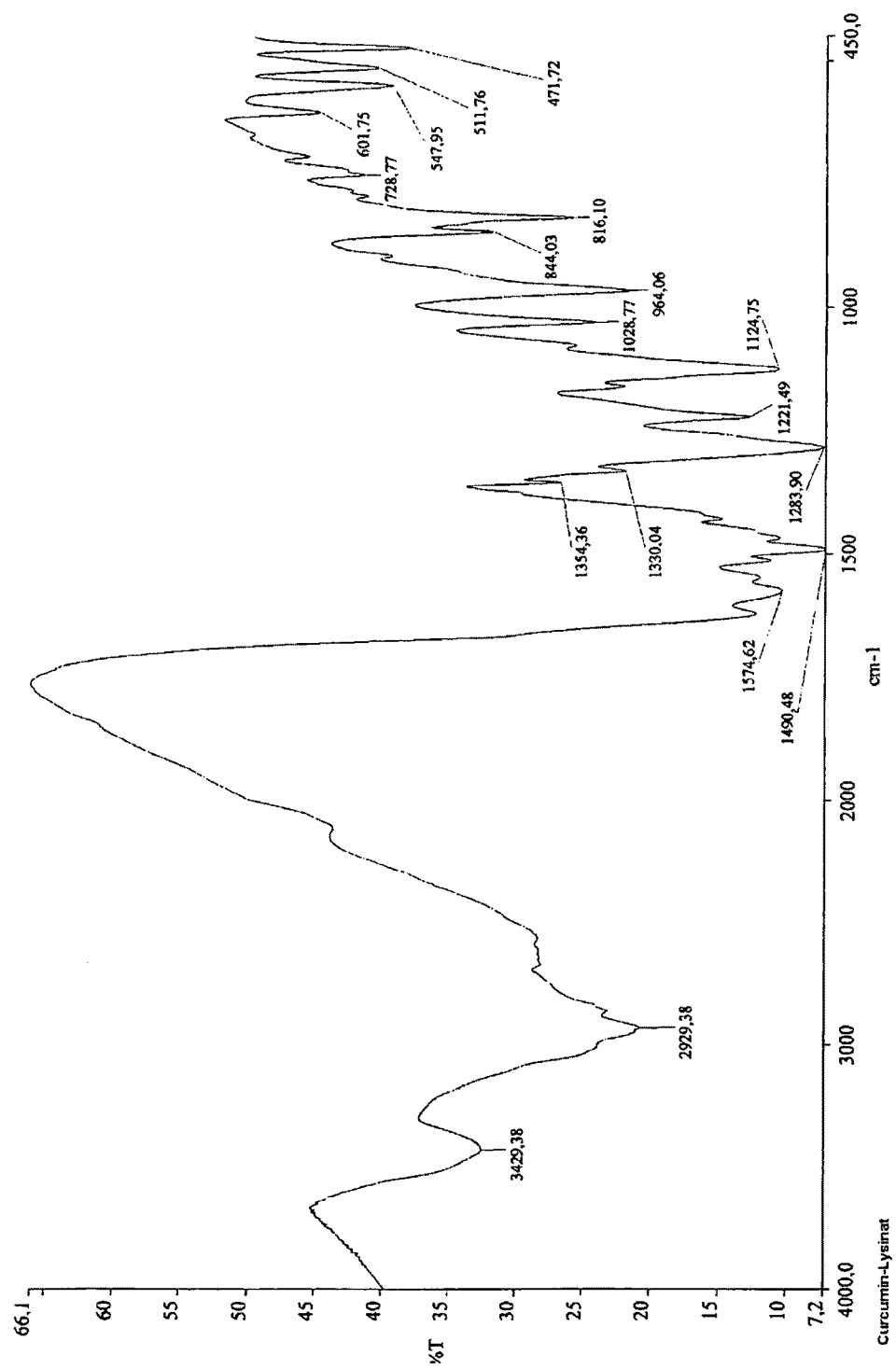
FIG. 7 represents a graph of the FTIR analysis of the curcumin lysinate composition of the invention.

FTIR (Fourier Transform Infrared Spectroscopy) Analysis: Apparatus: Perkin Elmer FT-IR Spectrometer Spectrum 1000, results see FIG. 6 (pure curcumin) and 7 (curcumin-lysinate) and data sets below.

| Pure Curcumin: (Kpa = 200.50 mg/S = 0.87 mg) | | | | | | | | |
|---|---|---|---|---|---|---|---|---|
| | 3551 | 4000.00 | 450.00 | 1.20 | 80.25 | 4.00 | %T | 8 | 2.00 |
| REF 4000 | 51.81 | 2000 | 78.82 | 600 | | | | |
| 3428.50 | 23.88 | 3021.60 | 51.02 | 2968.08 | 51.85 | 2923.80 | 36.31 | 2847.30 | 44.30 |
| 1627.14 | 5.58 | 1586.19 | 5.44 | 1514.97 | 1.20 | 1448.59 | 19.94 | 1426.30 | 19.40 |
| 1295.93 | 9.07 | 1266.59 | 3.71 | 1207.44 | 10.64 | 1186.48 | 24.45 | 1163.80 | 10.42 |
| 1144.41 | 9.87 | 1124.82 | 19.42 | 1030.06 | 34.24 | 968.97 | 19.01 | 842.72 | 29.02 |
| 818.04 | 38.25 | 775.33 | 53.56 | 729.18 | 71.50 | 600.70 | 52.76 | 551.75 | 48.50 |
| 469.72 | 51.42 | | | | | | | |
| END 26 PEAK(S) FOUND | | | | | | | | |

| Curcumin-Lysinate: (Kpa = 200.22 mg/S = 0.88 mg) | | | | | | | | |
|---|---|---|---|---|---|---|---|---|
| | 3551 | 4000.00 | 450.00 | 7.19 | 66.05 | 4.00 | %T | 8 | 2.00 |
| REF 4000 | 39.81 | 2000 | 49.90 | 600 | | | | |
| 3429.38 | 32.52 | 2929.38 | 20.71 | 1574.62 | 10.41 | 1490.48 | 7.18 | 1354.36 | 26.73 |
| 1330.04 | 21.94 | 1283.90 | 7.37 | 1221.49 | 12.83 | 1124.75 | 10.75 | 1028.77 | 24.24 |
| 964.06 | 21.73 | 844.03 | 31.85 | 816.10 | 25.84 | 728.77 | 41.44 | 601.75 | 44.73 |
| 547.95 | 39.36 | 511.76 | 40.40 | 471.72 | 38.06 | | | |
| END 18 PEAK(S) FOUND | | | | | | | | | pH in aqueous solution: +/−85 (1.10-5M), Apparatus Hanna Instrument HI8417

Thin Film Chromatography Analysis:

RF of the curcumin-Lysinat on TLC aluminium plates with silicium gel 60F-254 for a mobile choloroform-methanol phase (9.25:0.75 v/v) is 0.48.

C/ Preparation of Curcumin Lysinate in the Presence of hydroxypropyl-beta-cyclodextrin (HP-beta-CD)

Several solutions were prepared in order to determine the influence of HP-beta-CD on curcumin lysinate in terms of solubility and stability.

To achieve this, the method used was to vary the amounts of HP-beta-CD, to dose freshly prepared solutions with HPLC and to retain the latter for 24 hours at temperatures of 20° C. and 4° C., then to apply another dosage.

Four solutions were prepared. The quantities of curcumin lysinate were constant, 514 mg. the final volumes were also constant at 100 ml.

The quantities of HP-beta-CD were 1 g for solution N°1, 2 g for solution N°2, 3 g for solution 3 and 4 g for solution 4.

Conditions for Preparation of the Solutions:

In a graduated flask of 100 ml, the desired quantity of HP-beta-CD was weighted. 50 ml of distilled water were added and the resulting HP-beta-CD aqueous solution was then stirred during 5 minutes to achieve total solubility.

514 mg of curcumin lysinate were weighted. Curcumin lysinate was added—in one movement and under vigorous stirring—to the HP-beta-CD aqueous solution. 40 ml of distilled water were added and the solution was then stirred for 60 minutes. The gauge line was adjusted and the solution was homogenised.

The solution was filtered with Whatman 602H filter paper and a dosage by HPLC was performed. Several aliquots were prepared. Some of them were stored for 24 hours at 4° C. and others for 24 hours at 20° C. Before performing the second dosage by HPLC the aliquots were homogenised and filtered with Whatman 602H filter paper.

TABLE 1

Results of dosages

| | Concentrations of curcumin lysinate at Day 0 | Concentrations of curcumin lysinate at Day 1 (24 hours) at 4° C. | Concentrations of curcumin lysinate at Day 1 (24 hours) at 20° C. |
|---|---|---|---|
| Solution 1 (1 g HP-beta-CD) | $3.6\ 10^{-3}$ M | $3.6\ 10^{-3}$ M | $3.4\ 10^{-3}$ M |
| Solution 2 (2 g HP-beta-CD) | $4.5\ 10^{-3}$ M | $4.5\ 10^{-3}$ M | $4.4\ 10^{-3}$ M |
| Solution 3 (3 g HP-beta-CD) | $5.8\ 10^{-3}$ M | $5.8\ 10^{-3}$ M | $5.6\ 10^{-3}$ M |
| Solution 4 (4 g HP-beta-CD) | $7.6\ 10^{-3}$ M | $7.6\ 10^{-3}$ M | $7.3\ 10^{-3}$ M |

In conclusion, the solubility of curcumin lysinate in aqueous solution increases with concentration in HP-beta-CD. Curcumin lysinate is stable in aqueous solution (at 20° C.) and seems to be not influenced by concentration in HP-beta-CD.

D/ Influence of Lysine Base on the Solubility and Stability of Curcumin Lysinate in Aqueous Solution in the Presence of HP-beta-CD.

Solution N°4 was prepared under the conditions described above and 148 mg of lysine base was added during the solubilisation of HP-beta-CD.

In a graduated flask of 100 ml, the desired quantity of HP-beta-CD was weighted. 50 ml of distilled water were added and then 146.2 mg of L-lysine base. (1 eq) were added. The resulting solution was stirred for 5 minutes to achieve the total solubilization.

514 mg of curcumin lysinate were weighted. Curcumin lysinate was added—in one movement and while stirring well—to the aqueous solution of HP-beta-CD. 40 ml of distilled water were added. The so obtained solution was then stirred for 60 minutes. The gauge line was adjusted. The solution was homogenised and then filtered using Whatman 602H filter paper.

A dosage with HPLC was performed. Several aliquots were prepared. Some of them were stored for 24 hours at 4° C. and others for 24 hours at 20° C. Before performing the second dosage with HPLC the aliquots were homogenised and filtered with Whatman 602H filter paper.

TABLE 2

Results of dosages

| | Concentration of curcumin lysinate at Day 0 | Concentration of curcumin lysinate at Day 1 (24 hours) at 4° C. | Concentration of curcumin lysinate at Day 1 (24 hours) at 20° C. |
|---|---|---|---|
| Solution 4 (4 g HP-beta-CD) + Lysine | $1.10^{-2}$ M | $1.10^{-2}$ M | $8.10^{-3}$ M |

Limits of Solubility:

Several similar preparations were made in order to attempt to define the limits of solubility of curcumin lysinate in the presence of HP-beta-CD and of lysine base in aqueous phase.

In conclusion, increasing the concentration in Lysine base leads to an increase in the concentration of curcumin lysinate, but it does not influence the stability of curcumin lysinate in aqueous solution.

E/ Optimised Conditions:

1,028 g of curcumin lysinate was rendered soluble in 100 ml of distilled water in the presence of 6.56 g HP-beta-CD and of 292.4 mg of L-Lysine base. The concentration of curcumin lysinate in this solution was $2.10^{-2}$ M.

The compound according to the invention allows therefore to increase the solubility of curcumin derivatives in aqueous solutions which in turn enables IV administrations and/or increases their bioavailability. The table below presents the solubilities of the various intermediates.

The quantities of the NDS27 compound according to the invention needed to conduct experiments presented in examples 3, 4 and 5 were produced according to these optimised conditions.

F/ Influence of Lysine Base on the Solubility and Stability of Curcumin Lysinate in Aqueous Solution in the Presence of HP-Gamma-CD.

300 mg of curcumin lysinate was rendered soluble in 10 ml of distilled water in the presence of 787 mg HP-gamma-CD. (Wacker, lot 83P002)

Conditions for Preparation of the Solutions:

In a graduated flask of 10 ml, the desired quantity of HP-gamma-CD was weighted.

8 ml of distilled water were added and the resulting HP-gamma-CD aqueous solution was then agitated during 5 minutes to achieve total solubility.

300 mg of curcumin lysinate were weighted. Curcumin lysinate was added—in one movement and while agitating well—to the HP-gamma-CD aqueous solution. The gauge line was adjusted and the solution was homogenised.

Similar to the NDS27 composition, the use of the NDS28 curcumin salt complex in place of the pure curcumin improved greatly the solubility of the composition.

HP-gamma-CD curcumin lysinate (NDS27) and HP-gamma-CD curcumin lysinate (NDS28) could alternatively be lyophilised.

NDS27 and NDS28 according to the invention allow therefore to increase the solubility of curcumin derivatives in aqueous solutions which in turn enables IV administrations, by inhalation and/or increases their bioavailability.

Effects of orally administered NDS27 and NDS28 will be investigated in vivo in e.g. mouse model of metastatic dissemination.

TABLE 3

Results of solubilities

| | Water (20° C.) |
|---|---|
| curcumin | +/−0.0003 mg/ml |
| Curcumin-lysinate | +/−0.05 mg/ml |
| NDS27 | 10 mg/ml |
| NDS28 | >21 mg/ml |
| HP-beta-CD | 500 mg/ml |
| HP-gamma-CD | +/−500 mg/ml |
| Lysine | 640 mg/ml |

In conclusion, Curcumin lysinate and their cyclodextrin complexes NDS27 and NDS28 markedly increase the solubility of curcumin in water.

Example 3

In Vitro Stability of the NDS27 Compound

A solution of the NDS27 compound according to the invention with a concentration of $2.10^{-2}$ M of curcumin lysinate, was preserved for 50 days under temperatures of −20° C., 4° C. et 20° C. The dosages were conducted by HPLC.

TABLE 4

Results of dosages

| Initial molar concentration of curcumin lysinate | Molar concentration of curcumin lysinate after 50 days −20° C. | Molar concentration of curcumin lysinate after 50 days 4° C. | Molar concentration of curcumin lysinate after 50 days 20° C. |
|---|---|---|---|
| $2.10^{-2}$ M | $1.87\ 10^{-2}$ M | $3.5\ 10^{-3}$ M | $1.77\ 10^{-4}$ M |

Example 4

Administration of the NDS27 Compound According to the Invention in Rats (IP) and Ponies (IV)

We had firstly examined the behaviour of curcumin and its salts in the blood of different species. We had noted that if, in the blood of the rat or the rabbit, the stability is close to that observed in man, it is not the same for all species of animals examined. For example in the pig, the cow, the sheep and even the dog, as soon as mixed, there is a quasi total disappearance of curcumin. In the early stages we tested the toxicity by IP injection on rats then, taking into account the multiple points of similarity revealed between the blood of the horse and that of man, we decided to run trials on ponies.

A/ Intra-Peritoneal (I.P.) Administration of Compound According to the Invention in Rats A parent solution of the NDS27 compound according to the invention with a concentration of $1.10^{-2}$ M (5.14 mg/ml) of curcumin lysinate was produced.

The experiments were conducted using male <<wistar>> rats with an average weight of 250 g 0.5 ml of the parent solution, i.e. containing 2.54 mg of curcumin lysinate, was administered I.P. in a single dose. The absorption of the NDS27 compound according to the invention was studied after respectively ½ hour and one hour following the injection. A blood sample was taken from the abdominal aorta under total anaesthesia. The animal was then sacrificed. The blood dosage was then undertaken by HPLC according to the protocol described.

After ½ hour: 3.1% of the initially administered dose was detected. The abdominal fatty tissues were yellowish, leading to the assumption that the product diffuses slowly and passively. On the control rat, these tissues were white. The animal showed no behavioural abnormality and passed urine and faeces normally.

After one hour, 8.5% of the initially administered dose was detected. The abdominal fatty tissues were still slightly yellowish, leading to the assumption that the diffusion of the curcumin lysinate was not yet complete. The animal showed no behavioural abnormality and passed urine and faeces normally.

B/ Intravenous (I.V.) Administration of Compound According to the Invention in Ponies The first animal, aged 23 years, weighed 251 kg and a solution of the NDS27 compound according to the invention (with a concentration of $1.10^{-2}$ M of curcumin lysinate) duly rendered sterile and apyrogenous was injected at a rate of 1 l/hour for 2 hours. As from T 15 until T 120, the blood levels of curcumin were examined every ¼ hour and remained stable between 13 and 15 µM during one hour. After 75 minutes, these blood levels fell to around $10^{-7}$M and a further 15 minutes later, curcumin was no longer detectable.

During the entire operation, cardiovascular and behavioural parameters were followed. On the eve of the operation, during the operation and the following day, a general and complete biological examination was performed. Furthermore, all the blood parameters were examined on several occasions during the trial. No modification, even slight, was observed. Thus it appears that curcumin, even in the never previously attained blood levels of 13 to 15 µM generated no side effects. The dose of curcumin actually administered was 7.4 g.

A second experiment was conducted on a second pony aged 17 years and weighing 137 kg. The experiment consisted of administration of the solution of the NDS27 compound according to the invention (with a concentration of $1.10^{-2}$ M of curcumin lysinate) on the same rate (1 l/hour) for two hours and then doubling the rate of perfusion to reach levels that we hoped would approach 50 µM. Taking into account the difference of weight of the second animal, we expected blood levels of curcumin close to 20 to 25 µM during the first 2 hours and close to 50 µM during the third hour. This is effectively what occurred as, from T 15 to T 120, the blood levels of curcumin varied from 17.4 to 22.8 µM and from T 135 to T 180 from 49.9 to 48 µM, reaching a maximum of 53 µM at T 165. Fifteen minutes after the end of perfusion, the levels felt to 4.8 µM and felt below detectable limits at T 300. Once again all biological parameters were examined before, during and after the experiment without the slightest modification being observable. The dose of curcumin actually administered was 14.8 g. We believe that these experiments demonstrate for the first time the non-toxicity, at least in the acute phase, of curcumin, even at blood levels of the order of 50 µM.

A third experiment was conducted on a pony of around 170 kg, aged 15 years. A sterile and apyrogenous solution of the NDS27 compound according to the invention (with a concentration of $1.10^{-2}$ M of curcumin lysinate) was injected with a daily volume injected of 11 to 12 liters. The rate of injection was at first 1.5 l/h and then, taking account of the low blood levels of curcumin reached, it was increased to 2 l/h. The daily duration of the perfusion was about 6 hours and the plasma levels were regularly checked. Except during the first two hours of Day 1 when the rate of perfusion of 1.5 l/h gave 20 µM, the levels of curcumin in blood were in a range from 25 to 31 µM. The dose of curcumin actually administered was 169 g over 4 days, or 42 g/day. Once more it generated no suffering by the pony. Complete clinical and biological analyses were conducted before, during and up to 15 days following the experiment and the only observations worthy of interest were a slight lowering of the potassium concentration in the blood (during the perfusion with a return to normal values the following day after the end of perfusion) and a lowering of haemoglobin during the entire period of the perfusion with values returning to normal in the following days.

Example 5

Study of the Stability of Curcumin Lysinate in Solution in the Blood of Different Animal Species Preparation of a Parent Solution of Curcumin Lysinate
Weigh+/−precisely 5.14 mg of curcumin lysinate in a 100 ml flask
Bring up to the gauge line with methanol for HPLC.
Blood Sampling:
Venous blood from all the species studied was collected in citrated tubes and homogenised.
Collect 950 µL of blood. Add 50 µl of the parent solution of curcumin lysinate i.e. a final concentration of 5.10-5 M of curcumin lysinate.
Homogenise. Incubation time: one hour at 5° C., 20° C. and 37° C.
Preparations of the Samples for Dosages:
Following incubation each sample is centrifuged in order to obtain the PPP (Platelet Poor Plasma)
Conditions of preparation: 2000 G, Duration: 10 minutes, Temperature: 5° C. Centrifuge Eppendorf 5804R
100 µl pp of each sample is collected, to which is added 300 µl of methanol (precipitation of proteins).
Centrifuging: 10000 G Duration: 10 minutes Temperature 5° C.
The floating substance is dosed by HPLC.
Results of Dosages
Dog
Sample 5° C. below detectable limit
Sample 20° C. below detectable limit
Sample 37° C. below detectable limit
Cow
Samples 5° C. 1.10-5 M (20% of initial concentration)
Samples 20° C. below detectable limit
Samples 37° C. below detectable limit
Sheep
Samples 5° C. 1.10-5 M (20% of initial concentration)
Samples 20° C. below detectable limit
Samples 37° C. below detectable limit
Pig
Samples 5° C. 1.10-5 M (20% of initial concentration)
Samples 20° C. below detectable limit
Samples 37° C. below detectable limit
Horse
Samples 5° C. 4.9 10-5 M (98% of the initial concentration)
Samples 20° C. 2.45 10-5 M (49% of the initial concentration)
Samples 37° C. 2.0 10-5 M (40% of the initial concentration)
Rabbit
Samples 5° C. 4.7 10-5 M (94% of the initial concentration)
Samples 20° C. 2.1 10-5 M (42% of the initial concentration)
Samples 37° C. 1.55 10-5 M (31% of the initial concentration)
Man
Samples 5° C. 4.65 10-5 M (93% of the initial concentration)
Samples 20° C. 2.0 10-5 M (40% of the initial concentration)
Samples 37° C. 1.3 10-5 M (26% of the initial concentration)
Rat
Samples 5° C. 4.8 10-5 M (96% of the initial concentration)
Samples 20° C. 2.35 10-5 M (47% of the initial concentration)
Samples 37° C. 1.95 10-5 M (39% of the initial concentration).
In conclusion, the stability of curcumin lysinate changes in relation to the species that has been studied. It is also influenced by the temperature. Curcumin lysinate is poorly stable in the dog, the cow, the sheep and the pig, while it is stable in the horse, the human and the rat, in which it is also depending on the temperature.

Example 6

In Vitro Characterisation of the Biological Effects of the Compound According to the Invention A/ Effect on Overall Cell Growth
MTT tests were performed in order to rapidly, i.e. within 5 days, measure the effect of compounds of this invention on the overall cell growth. The test measured the number of metabolically active living cells that were able to transform the yellow product 3-(4,5-dimethylthiazol-2-yl)-2,5-diphenyl tetrazolium bromide (herein referred as MTT) into the blue product formazan dye by mitochondrial reduction. The amount of formazan obtained at the end of the experiment, measured by means of a spectrophotometer, is directly proportional to the number of living cells. Optical density determination thus enabled a quantitative measurement of the effect of the investigated compounds as compared to the control condition (untreated cells) and/or to other reference compounds.

Six human cancer cell lines described in Table 5 were used in the following MTT tests. These cancer cell lines cover six histological cancer types, being prostate, glioma, pancreas, colon, lung, and breast cancers.

To perform the assay, cells were allowed to grow in 96-well micro-wells with a flat bottom with an amount of 100 µl of cell suspension per well with 1,000 to 4,000 cells/well depending on the cell type used. Each cell line was seeded in its appropriate culture medium.

TABLE 5 human cancer cell lines

| Tumour cell lines | ATCC code | Tissue | Literature reference |
|---|---|---|---|
| PC3 | CRL-1435 | Prostate | Invest. Urol. 17: 16-23, 1979; Cancer Res. 40: 524-534, 1980 |
| U-373MG | HTB-17 | Glioma | Acta Pathol. Microbial. Scand. 74: 465-486, 1968 |
| BxPCS | CRL-1687 | Pancreas | Cancer Invest. 4: 15-23, 1986; Clin. Lap. Med. 2: 567-578, 1982 |
| LoVo | CCL-229 | Colon | Exp. Cell Res. 101: 414-416, 1976; J. Natl. Cancer Inst. 61: 75-83, 1978; Cancer Res. 39: 2630-2636, 1979 |
| A549 | CCL-185 | Lung | J. Natl. Cancer Inst. 51: 1417-1423, 1973; Int. J. Cancer 17: 62-70, 1976 |
| MCF-7 | HTB-22 | Breast | J. Natl. Cancer Inst. 51: 1409-1416, 1973 |

The detailed experimental procedure was the following: after a 24-hour period of incubation at 37° C., the culture medium was replaced by 100 µl of fresh medium in which the tested compound was previously dissolved, at the following molar concentrations: $10^{-9}$ M, $5.10^{-9}$ M, $10^{-8}$ M, $5.10^{-8}$ M, $10^{-7}$ M, $5.10^{-7}$ M, $10^{-6}$ M, $5.10^{-6}$ M, and $10^{-5}$ M. Each experiment was performed in sextaplicates.

After 72 hours of incubation at 37° C. with (experimental conditions) or without (control condition) the compound to be tested, the medium was replaced by 100 µl MTT dissolved in RPMI (1640 without phenol red) at a concentration of 1 mg/ml. The micro-wells were subsequently incubated during 3 hours at 37° C. and centrifuged at 400 g during 10 minutes. MTT was removed and formazan crystals formed were dissolved in 100 µl DMSO. The micro-wells were shaken for 5 minutes and read on a spectrophotometer at wavelengths of 570 nm (maximal formazan absorbance).

For each experimental condition, the mean optical density was calculated, allowing the determination of the percentage of remaining living cells in comparison to the control.

In this test we compared the cytotoxic effects of Tumeric (composed for 80% of curcumin, 15% of demethoxycurcumin and 5% of bis-demethoxycurcumin—which is the most usual commercial mixture enriched in curcumin), pure curcumin, tetrahydrocurcumin and the curcumin lysinate compound which represents the active moiety of the NDS27 compound according to the invention.

According to the literature, curcumin and curcumin derivatives have been shown to be poorly cytotoxic in this MTT test. Table 6 shows the $IC_{50}$ (representing the range of concentration of the compound tested that resulted in a 50% inhibition of overall tumour cells growth) for each compound in each cell line investigated; this $IC_{50}$ could only be reached with both curcumin and the NDS27 compound according to the invention on few cell line at high doses while the others compounds did not reach any $IC_{50}$. The dose-response profile of the active moiety (curcumin lysinate) of the NDS27 compound according to the invention is therefore comparable as to the one of curcumin itself and even appears to be slightly improved as compared to curcumin (FIG. 1).

TABLE 6

| Compound/ cell line | $IC_{50}$ (µM) values | | | | | |
|---|---|---|---|---|---|---|
| | A549 | PC3 | U-373MG | MCF-7 | LoVo | BxPC3 |
| Tumeric | >10 | >10 | >10 | >10 | >10 | >10 |
| Curcumin | >10 | >10 | 8.1 | >10 | 9.3 | 9.5 |
| Tetrahydrocurcumin | >10 | >10 | >10 | >10 | >10 | >10 |
| curcumin lysinate | >10 | >10 | 10 | >10 | >10 | >10 |

The curves of FIG. 1 illustrate the mean cytotoxic effect of each compound on the all 6 cell lines investigated B/ Impairment of Cell Proliferation and Cell Migration Triggered by the Compound of the Present Invention in Cancer Cells As the MTT test is based on the mitochondria functions, we also investigated the effects of curcumin (as reference) and the NDS27 compound according to the invention on cell proliferation, migration and morphology by means of a cellular imaging approach (Debeir et al., Cytometry 60:29-40, 2004; Debeir et al., IEEE Trans Med Imaging 24:697-711, 2005) either in an apoptosis-sensitive (U-373MG—see Table 4) as well as an apoptosis-resistant (PC3—see Table 4) cancer cell line. Cellular imaging relied on the use of computer-assisted phase-contrast microscopy making possible to film the behavior of living cells in culture dishes for several days.

Cells were seeded in a 25-cm² flask at a low density, treated or not with curcumin or the active moiety (curcumin lysinate) of the compound according to the NDS27 invention (at a concentration of 10 µM) and filmed thereafter for a period of 72 h. The experiment was conducted in quadruplicates.

The behaviour of the cells, in terms of morphology, growth/death and migration were thus investigated. The analysis of the films was performed by two operators, working independently. The effect on cell migration was characterized as +++ (high effect: cell migration of most cells is drastically altered for most of the duration of the film), ++ (medium effect: compound altering cell migration of an important proportion of the cells although less drastically), + (low effect: compound affecting cell migration of a small part of the cell population, or only for a limited part of the 72 h incubation), − (no effect: as compared to the control conditions, no difference is observed). The effect on cell morphology was characterized by the same way. The effect on the overall growth was measured by counting the number of cells on the first (0 h) and the last image (72 h) of each film. The global growth ratio (GGR) was then deduced by dividing the number of cells on the last image by the number of cells on the first image. The ratio $GGR_{treated\ cells}/GGR_{control\ cells}$, was further calculated thereby obtaining a value that describes the effect of compounds of the present invention on the overall cell growth.

Figure 2:
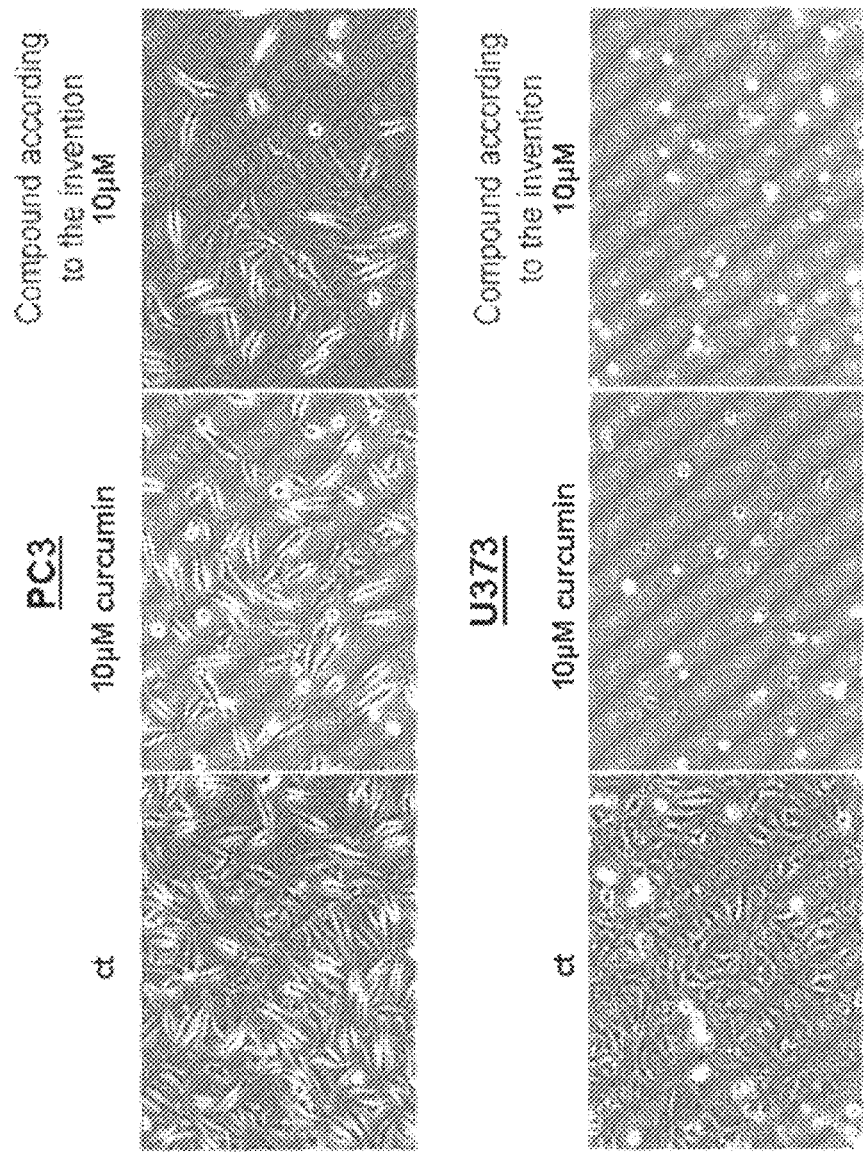
FIG. 2 presents illustrative phase contrast pictures obtained in an in vitro cellular imaging approach on cell lines untreated or treated with curcumin or the compound according to the invention.
Figure 3:
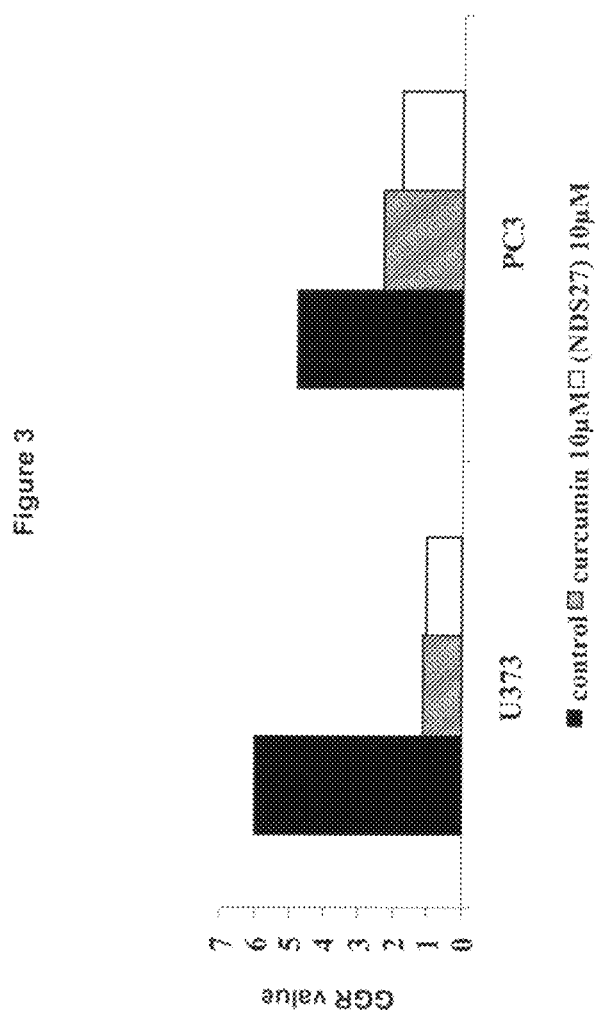
FIG. 3 presents the quantitative data obtained from FIG. 2 on cell lines untreated or treated with curcumin or the compound according to the invention.

The films (not shown) and data obtained clearly show that the compound according to the invention impairs cell morphology, proliferation and migration of human cancer cells. Illustrative pictures (time=72 h) of each cell line left untreated or treated with curcumin or the active moiety (curcumin lysinate) of the NDS27 compound according to the invention (10 µM) are provided in the FIG. 2 and assess a slight improvement of the cell growth inhibitory effect of the NDS27 compound according to the invention on the PC3 cell line as compared to curcumin. The GGR parameter analyses confirmed the marked impairment of cell growth in both cell lines with both reference (curcumin) and the active moiety (curcumin lysinate) of the NDS27 compound according to the invention (FIG. 3).

Table 7 summarizes all the data obtained with this assay; the NDS27 compound according to the invention clearly impairs cell morphology, migration and growth as curcumin do. Nevertheless, we observed a slight improvement of those effects with the NDS27 compound according to the invention as compared to curcumin and this could partly relate to its improved solubility which was the most hindrance for the therapeutical development of curcumin.

TABLE 7

Cellular imaging: recapitulative data

| Cell line compound | PC3 | | | U-373 MG | | |
|---|---|---|---|---|---|---|
| | effect on cell migration | effect on cell morphology | $GGR_{treated}/GGR_{control}$ | effect on cell migration | effect on cell morphology | $GGR_{treated}/GGR_{control}$ |
| curcumin | — | + | 0.5 | Growth and migration arrest; Rapid cell death | | 0.2 |
| curcumin lysinate | ++ | ++ | 0.4 | Growth and migration arrest; More rapid cell death | | 0.2 |

The study was performed using the NDS27 composition. However, given the even higher solubility of the NDS28 composition and its identical active ingredient curcumin lysinate, we expect to obtain at least similar results with the NDS28 compound.

Example 7

In Vivo Evidence of Anti-Cancer Activity of the NDS27 Compound According to the Invention To test the in vivo anti-cancer activity of the compound according to the invention, we made use of the SC-VII mouse head and neck orthotopic cancer model. SC-VII mouse head and neck cancer cells were cultivated in conventional culture medium containing supplementation in foetal calf serum and antibiotics (penicillin/streptomycin and gentamycin). 500 000 cancer cells were grafted in a serum free culture medium (50 µl) into the floor of the mouth of each mouse. 5 days after the graft, the 44 animals were divided into four groups of 11 mice. The treatments were as follows:
  Group 1: mice treated with the vehicle alone (HP-beta-CD—L-Lysine solution)
  Group 2: mice treated with cisplatin administered IP at the dosis of 5 mg/kg, 1 time per week during 3 weeks
  Group 3: mice treated IP with the NDS27 compound according to the invention administered 3 times per day, 5 days per week during 3 weeks at the doses of 20 mg/kg
  Group 4: mice treated with a combination of both treatments described for groups 2 and 3.

Figure 8:
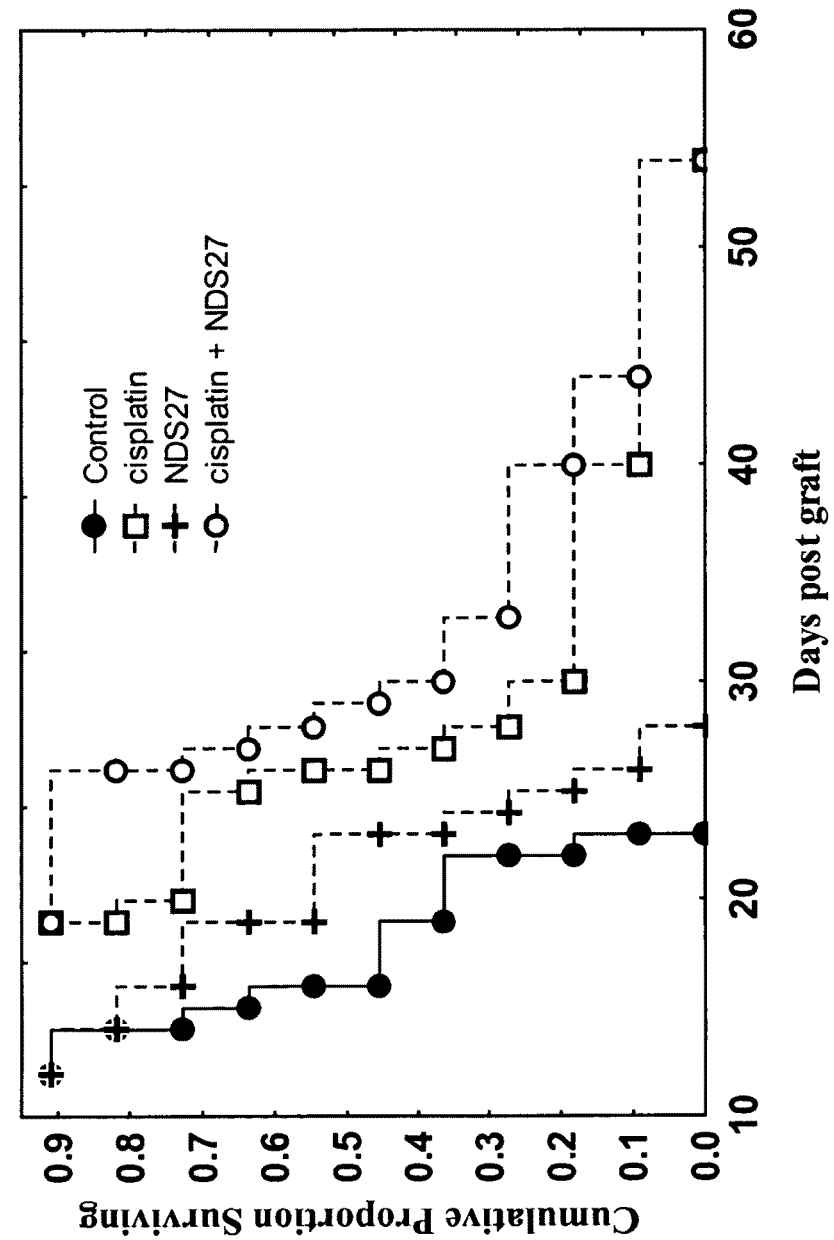
FIG. 8 represents the survival of mice bearing head and neck cancer left untreated or treated with cisplatin, which is the reference drug for this cancer, the compound according to the invention (NDS27 used) or combination of both treatments.

Mice were sacrificed when they lost 20% of their weight or when tumour reached 500 mm². Survival of the animals was followed and is illustrated in FIG. 8. Treatment of the mice with the compound according to the invention alone improved slightly but significantly the survival of the animals as compared to the control group: the T/C index, which relates to the ratio of the median survival period of mice treated with the compound to the one of the control group, was of 144% for the NDS27 compound according to the invention, meaning that the median survival was increased by 44% as compared to untreated mice. The cisplatin T/C index was of 163% and was significantly increased to 181% when combined with the compound according to the invention.

The therapeutic benefit of the NDS27 compound according to the invention, administered alone or in combination with chemotherapeutical agent such as cisplatin could however be improved with low release formulations. Accordingly, the short half-life of the NDS27 compound according to the invention could be increased by optimising formulation. Moreover, this mouse model is particularly aggressive: it leads to death of the animals within 25 days and is therefore difficult to treat. The study was performed using the NDS27 composition. However, given the even higher solubility of the NDS28 composition and its identical active ingredient curcumin lysinate, we expect to obtain at least similar results with the NDS28 compound.

Example 8

In Vivo Evidence of Anti-Cancer Activity of the HP-gamma-CD-Curcumin Compound According to the Invention Through Inhalation In order to develop a potentially useful preventive therapy, the type of administration of curcumin has been carefully examined and we have tested the consequences of inhaled curcumin on tumour dissemination. As control, we used oral administration of the cyclodextrin-curcumin complex and found surprisingly that these complexes originally designed to allow a sufficient bioavailability of curcumin by inhalation were significantly preventing tumour growth and dissemination. We further studied this phenomenon and have performed stability studies of the complex curcumin-cyclodextrin.

Therefore, effects of orally administered curcumin have been investigated in a mouse model of metastatic dissemination:
  Murine melanoma B16F10 cells stably transfected with a plasmid containing the luciferase cDNA have been injected subcutaneously into C57Bl/6 mice
  Mice are treated orally either with (hydroxypropyl-gamma-cyclodextrin) HP-gamma-CD 50 mM alone, which is used as a vehicle to solubilise curcumin and used as an internal control or with a solution of 1 mM curcumin solubilised in 50 mM HP-gamma-CD. Another group of mice has been treated with curcumin in suspension (not solubilised with the HP-gamma-CD complex). Treatment is performed on daily basis until sacrifice of the mice
  In vivo dissemination of cells has been regularly analyzed using the Xenogen Imaging System IVIS 200®. For this purpose, 100 µl of the luciferin-mix is injected intraperitoneally into each mouse. Melanoma cells containing the luciferase gene are viewable in vivo.

Figure 9A:
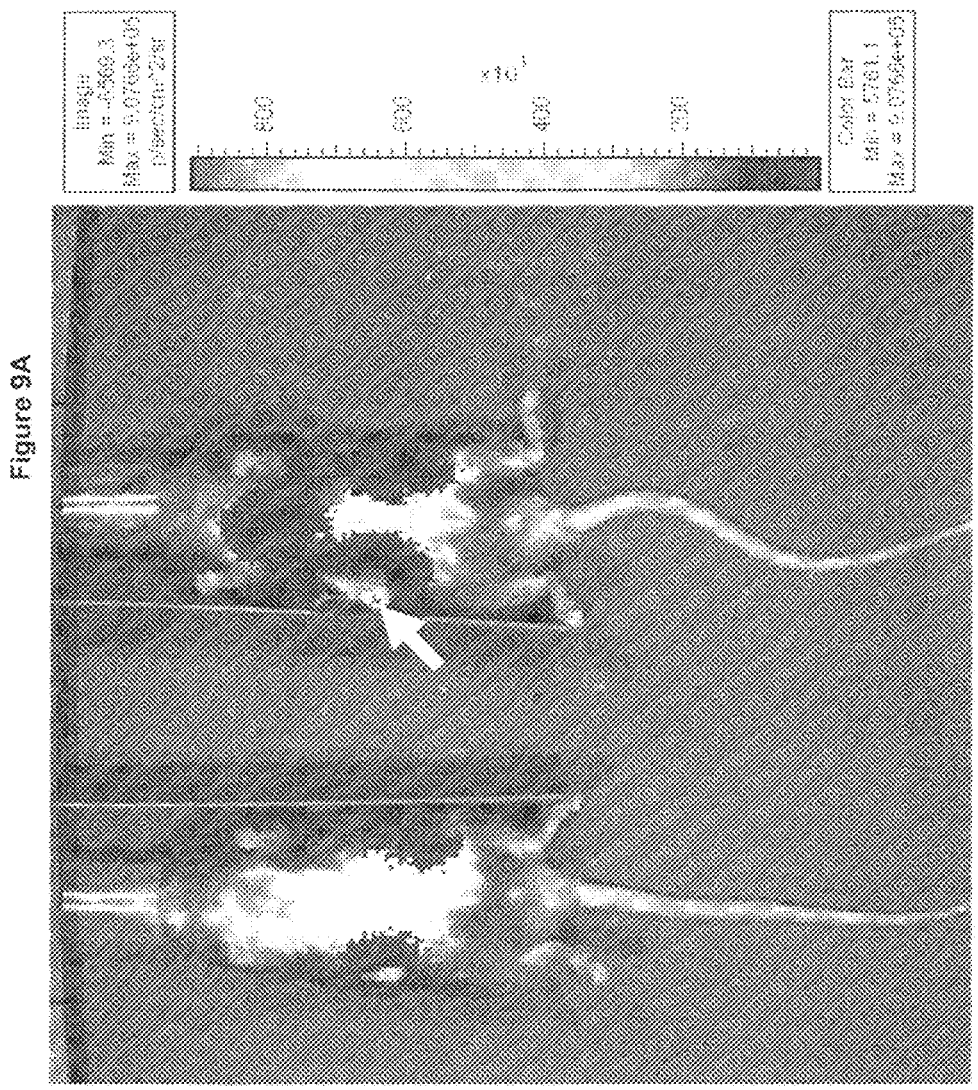
FIG. 9: Examples of the in vivo analysis with Xenogen IVIS® 200. Metastasis dissemination in mice treated either with HP-gamma-CD-curcumin (FIG. 9a), with the control HP-gamma-CD (FIG. 9b) or with a suspension of curcumin (FIG. 9c), 12 days after subcutaneous injection of melanoma cells.
Figure 10:
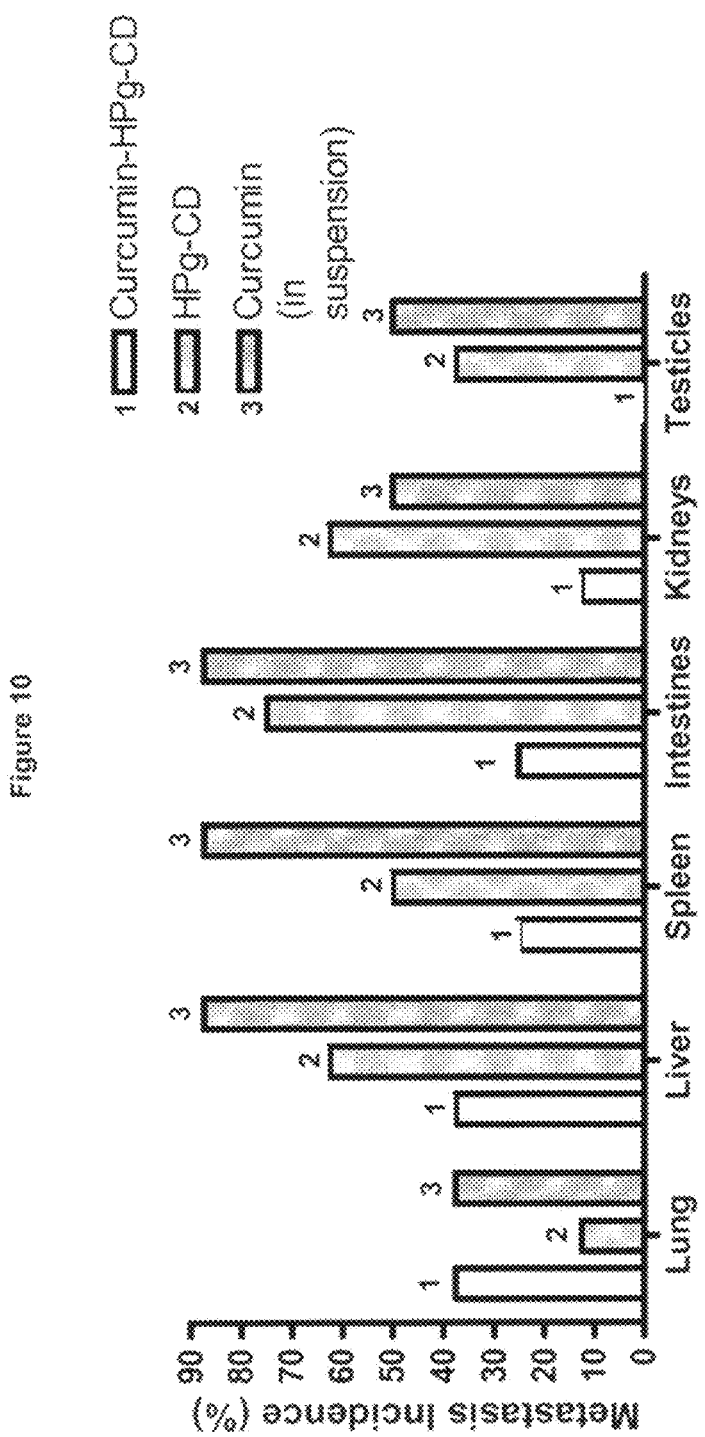
FIG. 10: Metastatic incidence in mice treated with curcumin-HP-gamma-CD, curcumin (suspension) or HP-gamma-CD alone.

First experiments have shown that mice orally treated with HP-gamma-CD-curcumin complexes displayed significantly less metastases than mice orally treated with HP-gamma-CD alone or curcumin itself (FIGS. 9 and 10).

Having these results in mind, we considered important to investigate the effects of orally administered curcumin on metastasis dissemination using other cell types. Therefore, different cell lines (Lewis Lung Carcinoma cells, 4T1 mammary cells) have been subcutaneously injected into mice and metastatic dissemination of cells has been analysed in vivo.

Also a model of primary lung carcinoma has been developed in our laboratory. For this, we can for example use a mouse strain (NJ, Jackson Laboratories) that develops a high incidence of spontaneous lung adenomas, and lung tumours readily develop in response to carcinogens, although alternative animal model systems known to the artisan can of course also be used. To induce development of lung tumours, mice have been injected twice with urethane. A curative or preventive model of treatment has been applied. Sacrifice of mice is planned when macroscopic adenoma have developed. The impact of curcumin administration on tumour development will be analysed by counting adenoma nodules present in the lungs.

The study was performed using the HP-gamma-CD-curcumin composition, indicating that the lysinate derivative thereof (called NDS28) as shown below, is expect to obtain at least similar results with the NDS28 compound in said in vivo experiments due to its higher solubility. Similarly, this experiment shows that not only beta-cyclodextrin derivatives have the ability to deliver the curcumin effect in vivo, but also the gamma-cyclodextrin derivatives are effective. This again shows that the cyclodextrin component or lysine or arginine component of the composition does not interfere with the biological activity of the composition as such, but alters the bio-availablility and in vivo delivery of the curcumin component as the active ingredient, through changes in solubility and stability.

Example 9

Solubility and Stability Studies of Different Curcumin Cyclodextrin Derivatives

1. Influence of Different Cyclodextrins

In order to test the solubility of curcumin, it was derivatised with one of the following cyclodextrins:
- beta-cyclodextrin (Cavamax W7 Pharma lot 70P277),
- alpha-cyclodextrin (Cavamax W6 Pharma Wacker 60P304),
- RAMEB Randomly Methylated cyclodextrins (Wacker, lot 71P015),
- HP-gamma-CD (Wacker, lot 83P002),
- Crismeb (roquette lot 765342)
- HP-beta-CD (wacker lot 74T003),
- beta-cyclodextrin (Cavamax W7 Pharma lot 70P277) plus alpha-cyclodextrin (Cavamax W6 Pharma Wacker 60P304)

Figure 11A:
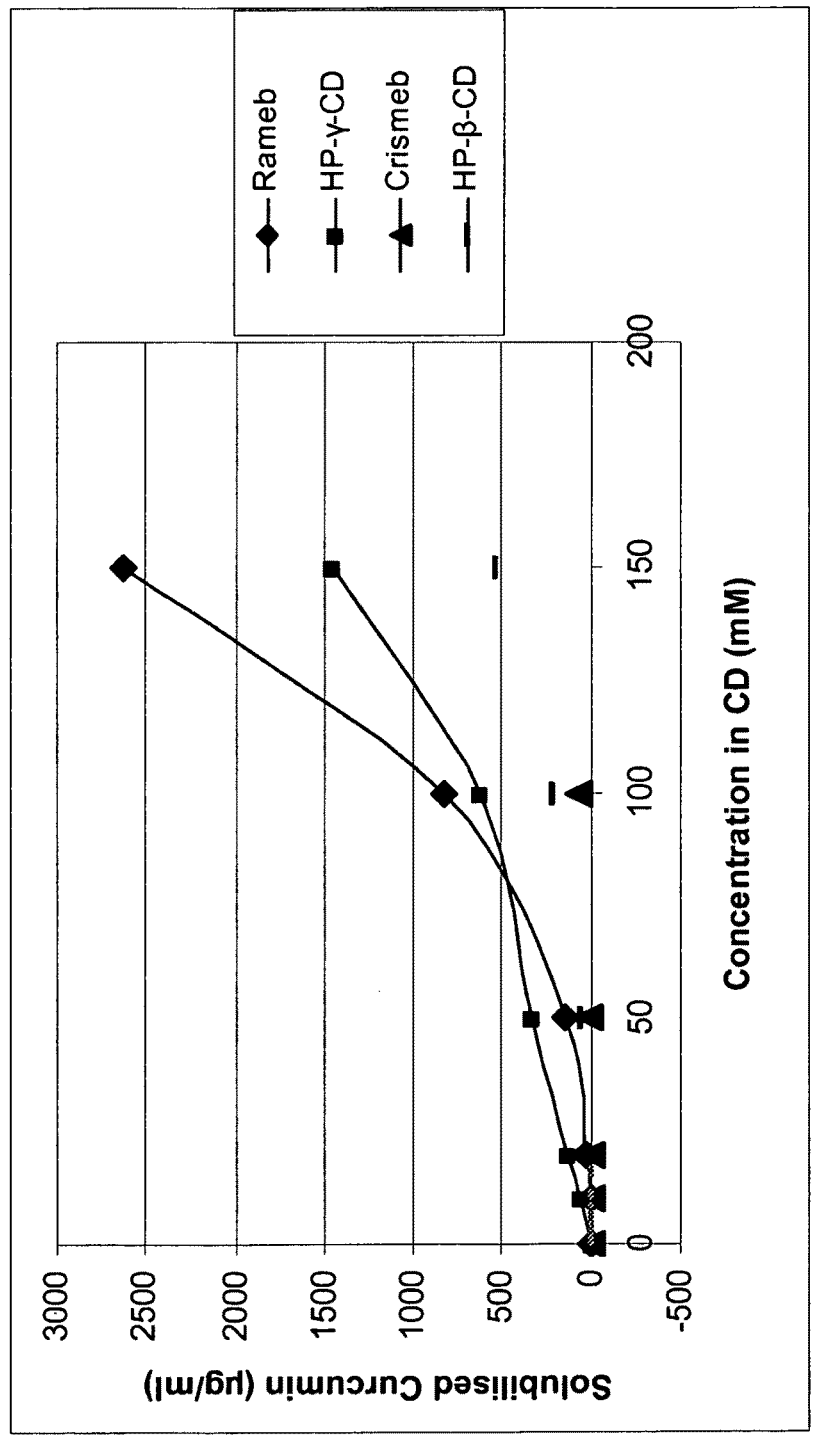
FIG. 11a displays the difference in curcumin solubility in combination with Rameb, Crismeb, HP-gamma-CD and HP-beta-CD, wherein Rameb, HP-gamma-CD and HP-beta-CD clearly increase the solubility of curcumin.
Figure 11B:
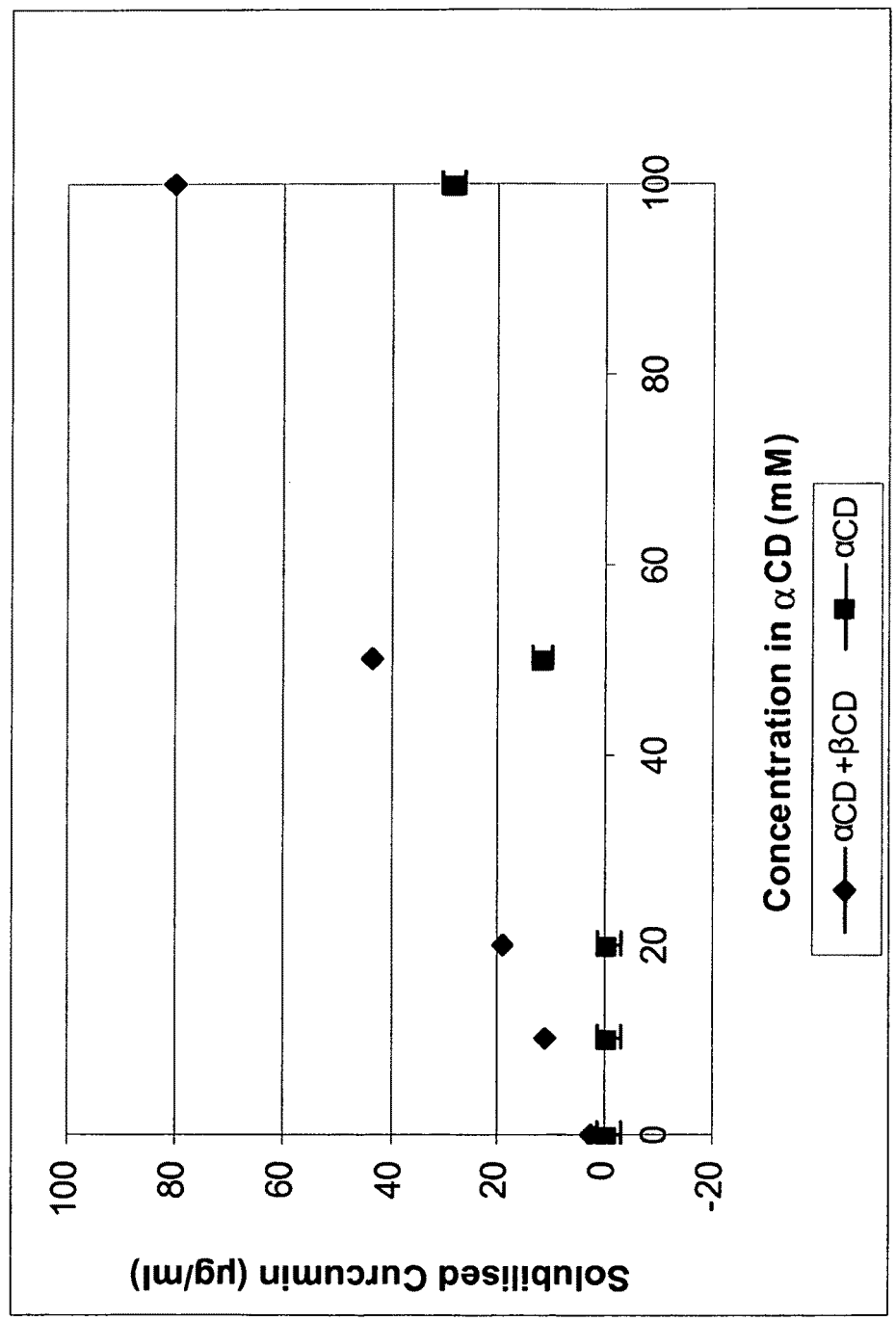
In FIG. 11b, the use of alpha cyclodextrin was compared to the use of a combination of alpha and beta cyclodextrins, the latter clearly increasing the solubility of curcumin.

The results are indicated in FIGS. 11a and 11b, which clearly show the effect of certain cyclodextrins on the curcumin solubility. Rameb, HP-gamma-CD and HP-beta-CD clearly increase the solubility of curcumin. In FIG. 11b, the use of alpha cyclodextrin was compared to the use of a combination of alpha and beta cyclodextrins, the latter clearly increasing the solubility of curcumin.

2. Influence of Different Concentrations of HP-Gamma-CD on Curcumin Solubility and Maintenance of Solubility Characteristics over Time.

Figure 12A:
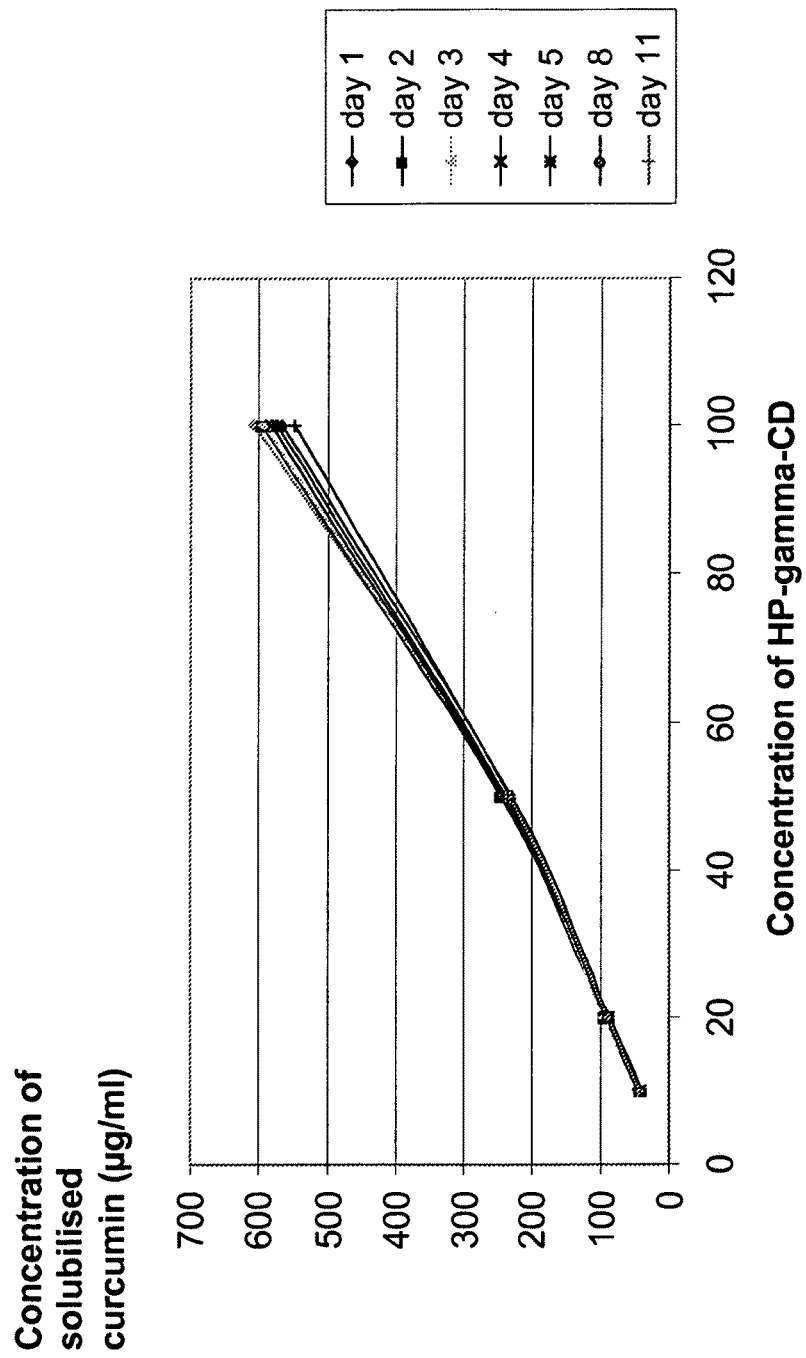
FIG. 12a shows the solubility when agitated after 1, 2, 3, . . . or 11 days after the mixture was made (T0). This graph shows that even after 11 days, the curcumin-HP-gamma-CD is still easily solubilised.

In FIG. 12a, the solubility of 50 mM HP-gamma-CD-curcumin was tested when mixed 1, 2, 3, . . . or up to 11 days after the initial preparation of the mixture (T0), indicating there is virtually no loss of solubility after 11 days.

Figure 12B:
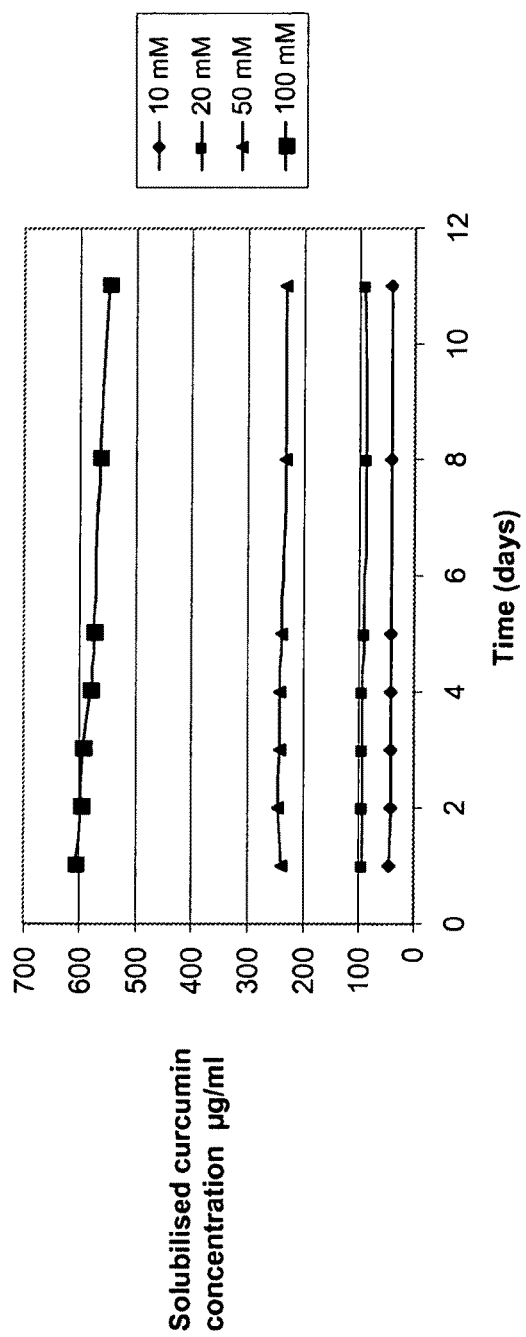
FIG. 12b shows the concentration of curcumin-HP-gamma-CD after 1, 2, 3, . . . 11 days after initial preparation, indicating its stability and solubility is maintained over the tested period.
Figure 15:
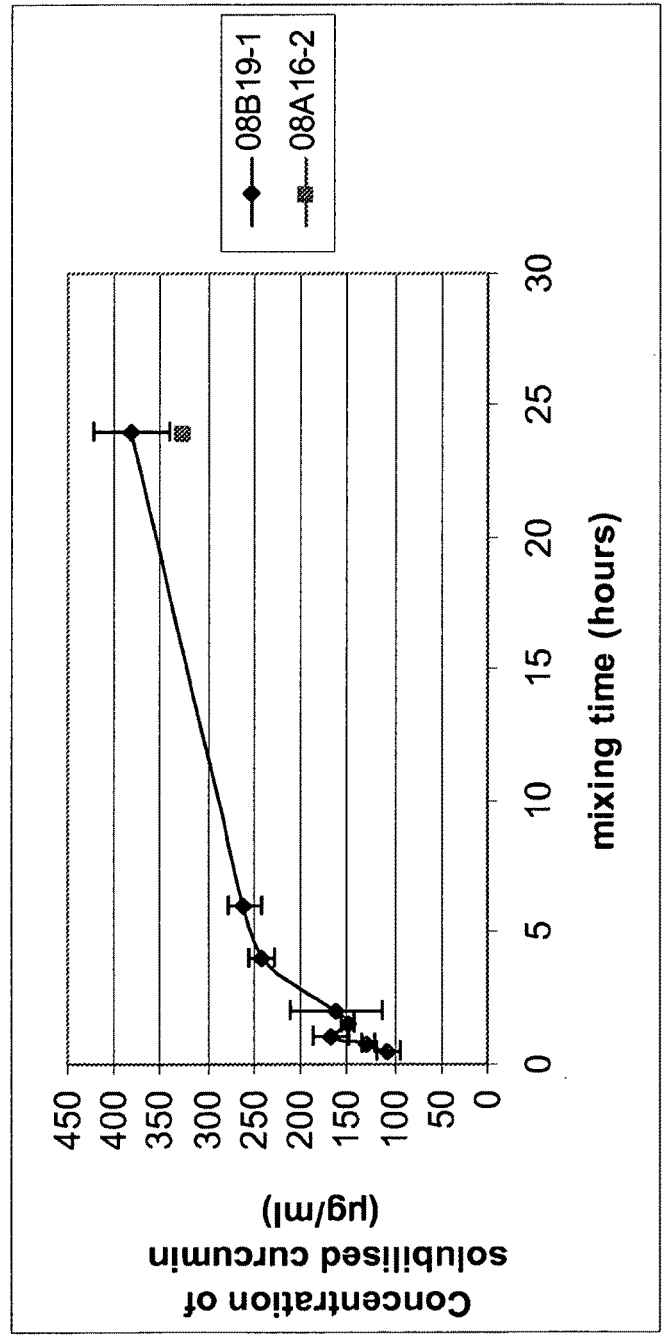
FIG. 15 shows the minimal mixing or agitation time needed in order to dissolve 1 mM curcumin and 50 mM HP-gamma-CD.

The influence of the concentration of HP-gamma-CD on curcumin solubility was also assessed (cf. FIG. 12b), indicating that up to 100 mM of curcumin can be easily solubilised and maintained soluble for a prolonged period.

3. Influence of Agitation Method on Curcumin Solubility

The results as depicted in FIG. 13 clearly indicate that the diode array method is outperforming the different types of water bath agitation methods.

4. Assessment of the Long Term Stability of Curcumin.

The stability of a 50 mM HP-gamma-CD-curcumin derivative was assessed at 25° C. for up to 14 days (cf. FIG. 14) and at 4° C. or −20° C. for up to 7 months (Table 8). These results indicate that the mixture is stable for at least 7 months, when kept at 4° C. or at −20° C. At 25° C., 80% of the curcumin-CD derivative is retained after 14 days.

TABLE 8

Stability at 4° C. and at −20° C.

| date | Stability at 4° C. and at −20° C. | | Surface HPLC peak | Concentration µg/ml | % | mM |
|---|---|---|---|---|---|---|
| Aug. 28. 2008 | T0 | 0 | 6003413 | 358.11 | 100 | 0.97 |
| Sep. 9, 2008 | | 4° C. | 6120095 | 342.15 | 95.54 | 0.93 |
| Sep. 9, 2008 | Frozen 1 months | at −20° C. | 6714374 | 374.92 | 104.69 | 1.02 |
| Oct. 2, 2008 | | 4° C. | 6062215 | 386.12 | 107.82 | 1.05 |
| Oct. 2, 2008 | Frozen 1 months | at −20° C. | 6028731 | 383.99 | 107.23 | 1.04 |
| | | | 6067928 | 386.49 | 107.92 | 1.05 |
| | | | 6054636 | 385.64 | 107.69 | 1.05 |
| Nov. 3, 2008 | | 4° C. | 5982526 | 382.06 | 106.69 | 1.04 |
| | | | 5957965 | 380.49 | 106.25 | 1.03 |
| Nov. 3, 2008 | Frozen 2 months | at −20° C. | 6462113 | 412.69 | 115.24 | 1.12 |
| | | | 6335614 | 404.62 | 112.99 | 1.10 |
| Dec. 3, 2008 | | 4° C. | 5987219 | 356.98 | 99.69 | 0.97 |
| | | | 6039497 | 360.09 | 100.55 | 0.98 |
| Dec. 3, 2008 | Frozen 3 months | at −20° C. | 6731034 | 401.17 | 112.03 | 1.09 |
| | | | 6503597 | 387.66 | 108.25 | 1.05 |
| Jan. 7, 2009 | | 4° C. | 5824913 | 377.50 | 105.42 | 1.03 |
| Jan. 7, 2009 | Frozen 4 months | at −20° C. | 6026952 | 390.60 | 109.07 | 1.06 |
| Feb. 3, 2009 | | 4° C. | 5527344 | 373.36 | 104.26 | 1.01 |
| Feb. 3, 2009 | Frozen 5 months | at −20° C. | 5892050 | 397.97 | 111.13 | 1.08 |
| Mar. 30, 2009 | | 4° C. | 5747237 | 361.19 | 100.86 | 0.98 |
| Mar. 30, 2009 | Frozen 7 months | at −20° C. | 6364896 | 400.01 | 111.70 | 1.09 |

In essence, these experiments show that HP-γ-CD-curcumin is very stable for a period of up to 7 months when stored at 4 or −20° C.

In Table 9 below, the filter retention of the curcumin-HP-gamma-CD was tested upon filtration using several membranes such as Millipore, Micropore etc. The results indicate the composition as such is not excessively lost upon sterilization by means of filtration.

TABLE 9 filtration experiment

| Concentration CD (mM) | Filtration | Surface HPLC | Concentration (µg/ml) | Mean |
|---|---|---|---|---|
| 50 | no | 424690 | 56.94 | 56.12 |
|  |  | 411946 | 55.30 |  |
| 50 | yes: micropore | 369552 | 49.85 | 49.36 |
|  |  | 361896 | 48.86 |  |
| 50 | yes: sterile hydrophile | 367150 | 49.54 | 48.98 |
|  |  | 358386 | 48.41 |  |

Similar results in stability were obtained for the curcumin lysinate complex with the HP-gamma-CD component (not shown).

5. Increased Water Solubility of Curcumin Lysinate Derivatives such as HP-β-CD-Curcumin Lysinate (NDS-27) and HP-γ-CD-Curcumin Lysinate (NDS-28).

In this example, the water solubility of the cyclodextrin complexes with curcumin lysinate was compared to solubility of the cyclodextrin complexes with pure curcumin. For this, 50 mM HP-gamma-CD was prepared.

With pure HP-gamma-CD-curcumin for example, an aqueous concentration of 0.368 mg/ml is easily reachable by stirring at room temperature, while under the same conditions, the HP-gamma-CD-curcumin lysinate easily resulted in a concentration of 21 mg/ml, which indicates a 57 fold increase in solubility using the same conditions. This 21 mg/ml is not even the end limit of solubility of the curcumin salt component, since at this concentration the liquid is still clear and no precipitate is formed after filtration through a G3 column.

When using the same conditions for the HP-beta-CD-curcumin lysinate, a concentration limit of 6 mg/ml is easily reached, again a 20 fold increase of curcumin component as compared to the non-lysinated curcumin-cyclodextrin complex.

Preferably, the curcumin used in these experiments is synthetically made and not an extract having only about 75% actual curcumin content.

These results indicate that:
The lysine salt of curcumin is compatible with both the HP-beta-CD and the HP-gamma-CD.
The water solubility of curcumin lysinate is strongly increased by both the HP-gamma-CD and HP-beta-CD complexes.
The water solubility of the HP-gamma-CD complex (NDS28) is higher than that of the HP-beta-CD (NDS27) and thus results in a higher curcumin concentration in water.

Example 10

Effect of NSD-27 on Inflammation: a Study in Horses with Recurrent Airway Obstruction (RAO)

Study Objectives

The aim of this preliminary experimental protocol is to assess, in vivo, the possible anti-inflammatory effects of the inhaled curcumin in horses. Therefore, curcumin will be administered by inhalation during 7 consecutive days. The absence bronchospasm induced by the drug+Excipient inhalation will be controlled by the measurement of the mechanics of breathing. As well, the possible effects on the inflammatory status in horses suffering from recurrent airway obstruction (RAO) will be assessed by the follow-up of the cytology of the BAL (total cells count and neutrophils percentage) during the treatment. Myeloperoxidase in the BAL, which has been demonstrated to be a marker of neutrophil activation, will be also used to control the level of inflammation in the lower airways.

Material and Methods

Tests Animals:

Six horses suffering from a RAO are used. An exacerbation of their condition is induced by a natural challenge (hay and straw). The same environmental conditions are maintained during the whole inhalation protocol. The horse's respiratory condition is assessed on the basis of in-depth clinical examination, analysis of the arterial blood gases tensions, endoscopy of the respiratory tract, cytology of the broncho-alveolar lavage, and pulmonary function test evaluating the mechanics of breathing.

Measurements

Tests of Pulmonary Function:

Lung function (airway permeability and compliance) is tested using the forced oscillation technique (IOS: impulse oscillometry system). This technique measures respiratory resistance and reactance from 5 to 35 Hz during spontaneous breathing. It has been previously validated in horses (van Erck et al, Equine Vet J, 2004 & 2006). Samples of arterial blood are taken by puncture of the carotid artery, collected on heparinised syringes and analysed with a blood gas analyser to evaluate the gas exchange.

Broncho-Alveolar Lavages:

Horses are pre-medicated intravenously with romifidine (0.01 mg/kg). Lavage are done with the help of a video-endoscope of 2.6 m length and 9 mm diameter (Pentax, The Netherlands), the tip of which is introduced in the lower airway until wedged into a bronchi. Two syringes containing 60 ml of physiological serum at body temperature and a syringe containing 20 ml of air to empty the biopsy canal are successively sent to the blocked region, via the biopsy canal of the endoscope. The liquid is retrieved by gentle aspiration. An aliquot is reserved for cytology. Total cell count is performed manually using a Thoma cell. Specimens are prepared by cytospin (Thermoelectrocorporation, Shandon, Pittsburgh, Pa.) (800 revolutions per minute for 15 min) and stained with May-Gruenwald. Differential cell counts are determined by examination of 200 leukocytes per slide. Within 15 min after sampling, the remaining of BAL is centrifuged at 1000 g 10 min at room temperature. The supernatant is kept frozen in small aliquots at −20° C. until myeloperoxidase analysis and curcumin concentration assay.

Protocol

The 6 horses are randomly distributed into 2 groups of 3 individuals. For this first preliminary test (7 consecutive days), the group 1 inhales curcumin, and the group 2 an equivalent volume of the solution used for curcumin dilution (e.g. saline). Curcumin is administered by inhalation at the dose of 0.5 mg/100 kg of NDS27 (hydroxypropyl-beta-cyclodextrin salt of curcumin lysinate) in 5 ml of saline, at a dose of 4 mg/inhalation The administration will be carried out in a well ventilated local with positive pressure, in order to avoid aerosol inhalation by the technician. In addition, the technician will be wearing a medical mask. The inhalation will be repeated twice a day during 7 consecutive days.

Experimental Schedule

Basal pulmonary function tests, arterial blood gas analysis (ABG), and BAL are performed on D1. PFT are repeated at D1 and D7, before and 15 (D7+15) minutes after the first inhalation.

On D7, 30 minutes after the last inhalation, a BAL is performed. Both BALs serve for cytology and MPO concentration, and the BAL of D7 is also for curcumin concentration determination in the treated horses.

The horses were kept in the same environmental conditions for four days following the discontinuation of the treatment. AT this point (D7+4) PFT and BAL were repeated.

3. Results 3.1. Animals:

Five of the six horses exposed to a dusty environment developed clinical signs consistent with RAO after 7 to 52 days of exposure. One horse did not develop clinical signs during the 60 days exposure period and was withdrawn from the protocol. Initially three horses were included in the Curcumin group and two horses in the Excipient group (Table 10).

TABLE 10

Particulars of and exposure periods of the horses treated with either 7 days of Curcumin or 7 days of Excipient only

| Animal | Sex | Age | Start of exposure | Exposure period before treatment | Start of treatment | End of treatment | Treatment Group |
|---|---|---|---|---|---|---|---|
| Alix | F | | 07/02 | 39 | 19/03 | 26/03 | Curcumin |
| Kurry | M | | 26/01 | 52 | 19/03 | 26/03 | Excipient |
| Lola | F | | 05/02 | 7 | 12/02 | 19/02 | Excipient |
| Nouga | F | | 21/01 | 21 | 12/02 | 19/02 | Curcumin |
| Springy | M | | 21/01 | 21 | 12/02 | 19/02 | Curcumin |

3.2. Clinical Score:

The heaves score indicates a subjective score from 0 to 10 for the movement intensity of the nostrils and the abdominal wall, where 0 is normal breathing pattern and 10 is the most severely imaginable dyspnoeic pattern.

All of the treated horses improved their heaves score during the treatment and showed four days after discontinuation of the treatment a heaves score that was still lower than the initial score before treatment and lower or equal than the score after treatment. From the two horses of the Excipient group, one improved its heaves score and one, aggravated its heaves score. Details are displayed in table 11.

TABLE 11

Heaves scores of the horses treated with either 7 days of Curcumin or 7 days of Excipient only.

| | Group | Rem | D 1 | D 7 | D 7 + 4 |
|---|---|---|---|---|---|
| Alix | Curcumin | 0 | 8 | 4 | 3.5 |
| Lola | Excipient | 0 | 6 | 3.5 | 3 |
| Kurry | Excipient | 0 | 4 | 5.5 | 6 |
| Nouga | Curcumin | 0 | 6.5 | 4.5 | 2.5 |
| Springy | Curcumin | 0 | 4 | 2.5 | 2.5 |

3.3. Pulmonary Function Test (IOS):

The absolute values of the pulmonary function test a highly influenced by the tight fitting of the mask, however the values of the R5/R10 ratio, measured under the same conditions and during the same period of time are a highly stable constant indicating lower airway resistance.

Four of the five horses had a higher R5/R10 ratio after exposure to dusty environment (inclusion criteria). The remaining horse did not show any change in the R5/R10 ratio, neither after exposure, nor after treatment with Curcumin. The other two horses of this group showed either clear improvement or no change after treatment. Of the Excipient group, one horse showed an improved R5/R10 ratio the other horses an aggravated one. All horses, whether inhaling Curcumin or Excipient only, showed improved lung function, 15 minutes after inhalation. Details are displayed in table 12.

TABLE 12

R5/R10 ratio in horses treated with either 7 days of Curcumin or 7 days of Excipient only

| | | Rem | D1 | D7 | D7 + 15 | D7 + 4 |
|---|---|---|---|---|---|---|
| Alix C | Curcumin | 0.725 | 1.598 | 1.272 | 1.106 | 1.555 |
| Lola P | Excipient | 0.767 | 1.417 | 0.789 | 0.608 | 0.922 |
| Kurry P | Excipient | 1.005 | 1.349 | 2.068 | 1.271 | 1.287 |
| Nouga C | Curcumin | 0.957 | 1.412 | 1.383 | 1.170 | |
| Springy C | Curcumin | 0.725 | 0.756 | 0.812 | 0.739 | 0.773 |

3.4. Partial Pressure of Oxygen in Arterial Blood

The two horses of the Excipient group had higher paO2 values after exposure than in remission. After treatment with Excipient, the paO2 value was higher in one horse and lower in the other one, when comparing to values before treatment.

All horses of the Curcumin group had lower paO2 values after exposure. After treatment two horses showed higher paO2 values, and in the other two paO2 did not change (table 13).

TABLE 13

Partial pressure of oxygen from arterial blood samples from horses treated with either 7 days of Curcumin or 7 days of Excipient only.

| | Rem | D 1 | D 7 |
|---|---|---|---|
| Alix C | 85 mmHg | 62 mmHg | 100 mmHg |
| Lola P | 86 mmHg | 92 mmHg | 98 mmHg |
| Kurry P | 83 mmHg | 88 mmHg | 84 mmHg |
| Nouga C | 92 mmHg | 86 mmHg | 85 mmHg |
| Springy C | 85 mmHg | 76 mmHg | 93 mmHg |

3.5. Cytology:

From the Excipient treated horses, one horse showed increased neutrophils count during treatment, and the neutrophil count remained stable thereafter, while the other one did not show a changed neutrophil count during treatment but increased the neutrophil count thereafter. The Curcumin treated horses showed lower neutrophil count after treatment and an increase four days after discontinuation of treatment. However, the neutrophil count four days after treatment was still lower than before treatment (table 14).

TABLE 14

Neutrophil proportion (%) in BALF from horses treated with either 7 days of Curcumin or 7 days of Excipient only

| Horse | D 1 | D 7 | D 7 + 4 |
|---|---|---|---|
| Nouga C | 37.6 | 15.8 | 25.5 |
| Lola P | 37.4 | 57.3 | 56.4 |
| Springy C | 29.8 | 21 | 40 |
| Alix C | 27.1 | 15.9 | 16.8 |
| Kurry P | 34.1 | 32 | 49.1 |

3.6. Myeloperoxidase (MPO):

Plasmatic MPO was measured before and after treatment. In the two Excipient treated horses one had a higher plasmatic MPO value and one horse had a lower plasmatic MPO value after the treatment, when compared to the pre-treatment values. From the Curcumin treated horses, two had higher plasmatic MPO values and one horse had a lower plasmatic MPO value after treatment.

The MPO concentration in the broncho-alveolar lavage fluid (BALF) was measured before and after treatment, and four days after discontinuation of the treatment while the horses were kept in the same conditions. All horses had lower BAL MPO concentrations after the treatment, however, the decrease was more pronounced in the Curcumin treated horses than in the Excipient treated horses (table 15).

TABLE 15

MPO concentration (ng/ml) in plasma and BALF from horses treated with either 7 days of Curcumin or 7 days of Excipient only

| Horse | Group | Plasmatic MPO D1 | Plasmatic MPO D7 | BALF MPO D1 | BALF MPO D7 | BALF MPO D7 + 4 | BALF ENE D1 | BAL FENE D7 | BAL FENE D7 + 4 |
|---|---|---|---|---|---|---|---|---|---|
| Alix C | Curcumin | 186 | 94 | 34 | 8 | 0.14 | 18.075 | 11.3 | 9.071 |
| Kurry P | Excipient | 124 | 116 | | | 49.4 | 16.1 | 8.645 | 14.83 |
| Nouga C | Excipient | 312 | 1920 | 17.7 | 0 | 29.2 | | | |
| Lola P | Curcumin | 336 | 459 | 60 | 47 | 21 | 17.48 | 31.27 | 15.45 |
| Springy C | Curcumin | 86 | 1016 | 24 | 6 | 97 | 11.815 | 11.485 | 8.47 |

3.7. Treatment after Washout in One Horse

The horse of the Excipient group that showed aggravation of clinical signs during the Excipient inhalation period was treated with seven days Curcumin inhalation. The Curcumin treatment was performed with the same doses and regimens as in the initial Curcumin group. Treatment was started after a four days washout period, during which the horse was exposed to the same dusty environmental conditions. This horse showed improvement of the heaves score (D1:8; D7:6; D7+4:6) and the BALF neutrophil concentration (D1:49%; D7:24%; D7+4:31%). However, no improvement was observed in the R5/R10 ratio of the IOS measurements (D0: 1.00; D1: 1.66; D7: 1.75 D7+4: 1.66). Partial oxygen pressure of the arterial blood and plasmatic and BALF MPO concentrations were not determined in this horse.

4. Conclusion

Exposure periods and clinical signs were highly variable among the horses and one horse failed to show typical clinical signs within an extended exposure period. One horse did not show increased R5/R10 ratio at the beginning of the treatment. However, broncho-constriction as indicated from the heaves score and from the R5/R10 ratio were part of the inclusion criteria. This particular horse did not show any change in the R5/R10 ratio throughout the protocol. Two horses from the Excipient group had higher paO2 values after exposure than during remission.

Despite the technical difficulties related to the clinical evaluation of the horses, it can be stated that an obvious clinical improvement was observed in the three NDS27-treated horses and in one CD treated horse.

In conclusion, the three NDS27-treated horses showed a significant reduction in BALF neutrophil count and this reduction was related to a reduction in BALF MPO and Elastase concentrations. The study was performed using the NDS27 composition. However, given the even higher solubility of the NDS28 composition and its identical active ingredient curcumin lysinate, we expect to obtain at least similar results with the NDS28 compound.

Example 11

Effects of NDS27 on Isolated Activated Neutrophils

The inflammation response to various pathologies involves frequently an excessive stimulation of the polymorphonuclear neutrophils releasing reactive oxygen species (ROS) and myeloperoxidase (MPO).

This study showed the effects of NDS27, curcumin lysinate, pure curcumin and the different controls (cyclodextrin, lysine) on isolated neutrophils stimulated by phorbol myristate acetate (PMA) and on the activity of purified MPO.

The ROS production and the release of MPO by activated neutrophils were measured by chemiluminescence and ELISA techniques, respectively (Franck et al., 2008, Physiol. Res. 57(4):577-87). The activity of purified MPO was measured by using an original method called SIEFED (specific immune extraction followed by enzymatic detection) allowing the study of drug interaction with the enzyme without interferences of the medium (Franck et al., 2006, J Vet Diagn Invest, 18(4):326-34).

NDS27, curcumin lysinate and pure curcumin had dose-dependent inhibitory effects on ROS production and MPO release by activated neutrophils and on purified MPO activity. Curcumin lysinate had the same effects as pure curcumin. The controls, lysine and cyclodextrin, didn't have any effect on the activated neutrophils.

Figure 16:
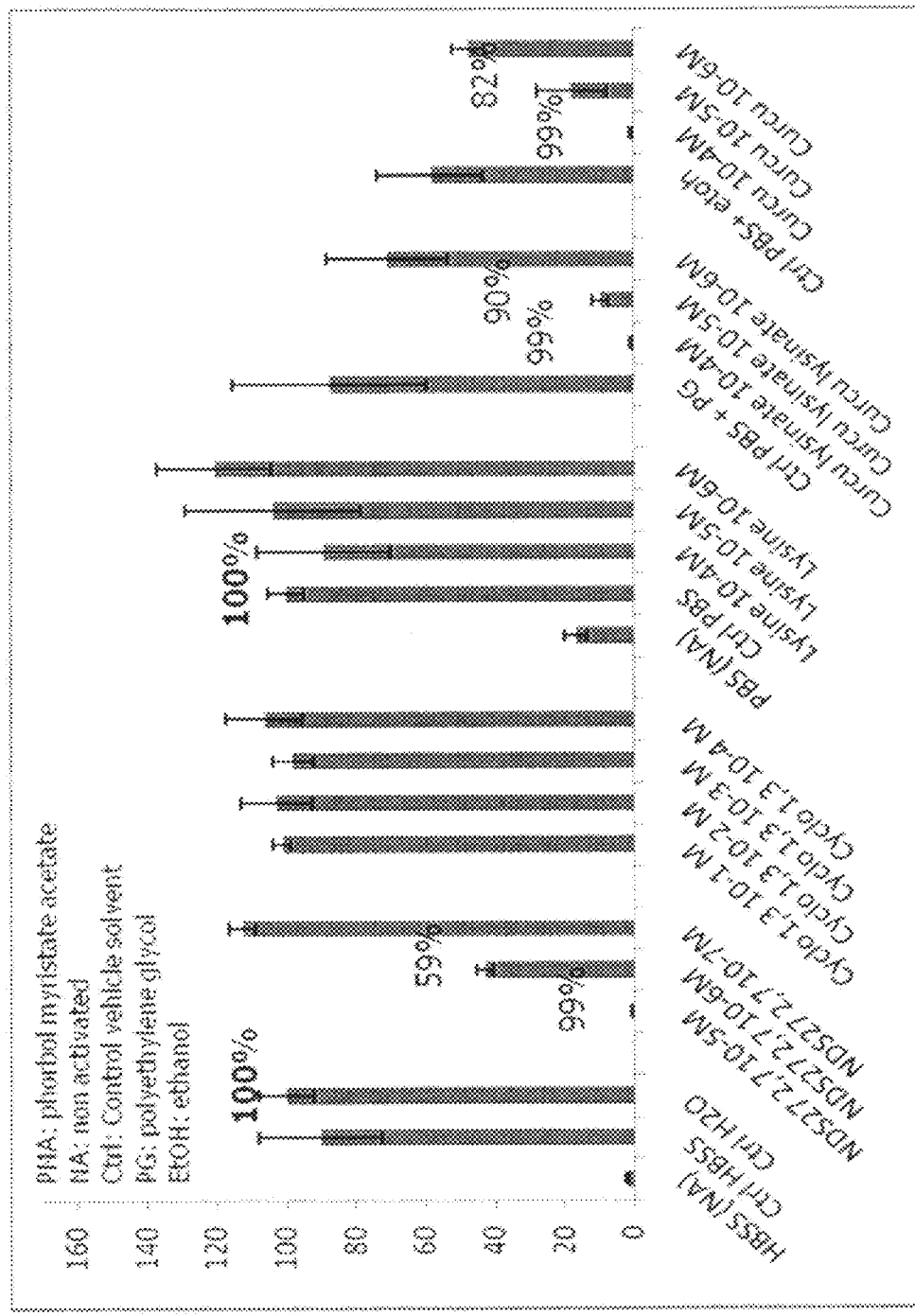
FIG. 16 shows the inhibitory effects of ROS release by stimulated neutrophils by PMA measured by chemiluminekence.

Nevertheless, NDS27 showed unexpected properties in this protocol:

A more potent inhibitory effect on the ROS release by stimulated neutrophils by PMA measured by chemiluminescence compared to curcumin lysinate and pure cucumin (FIG. 16).

Figure 17:
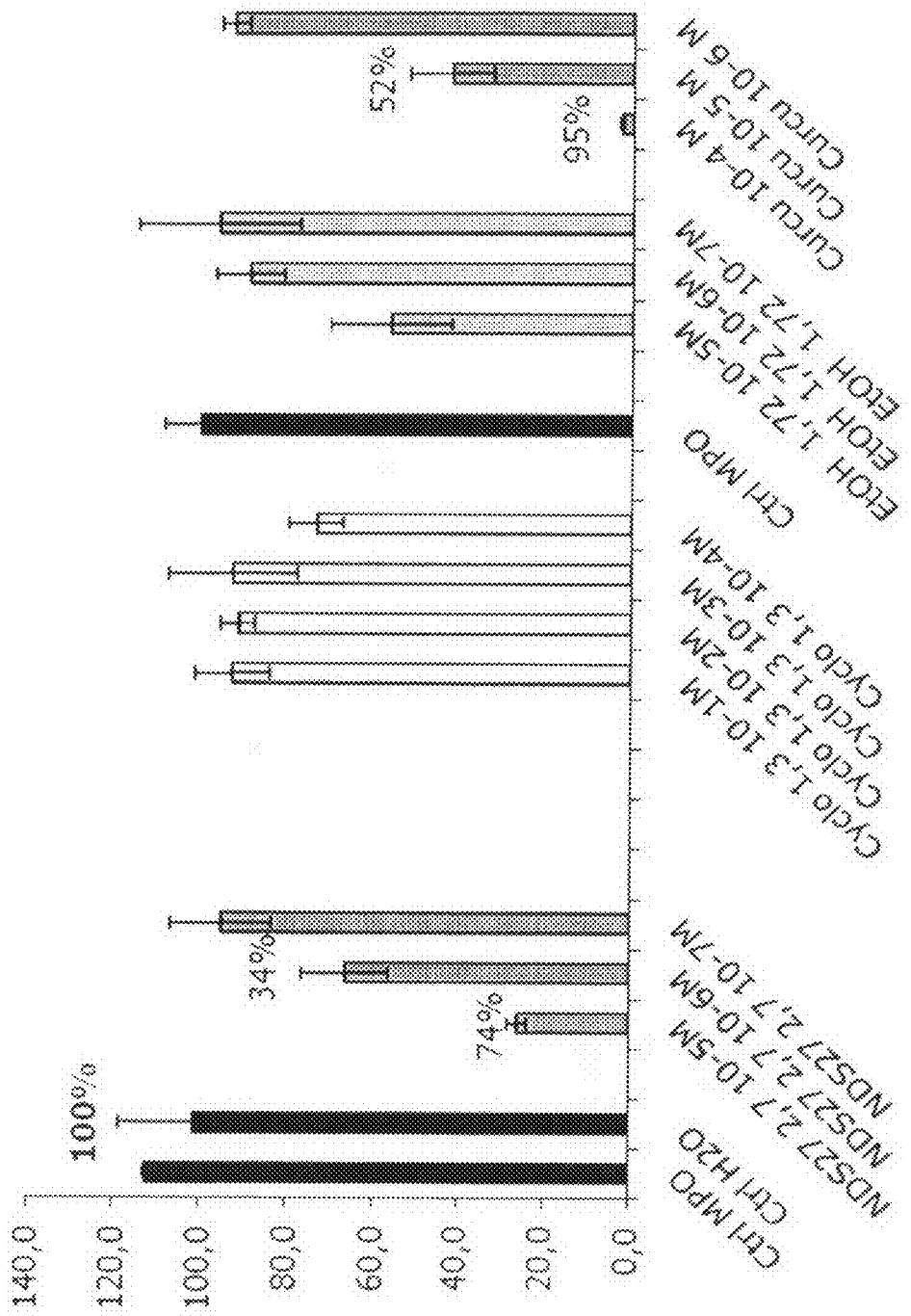
FIG. 17 shows the inhibitory effects of NDS27 and pure curcumin on the activity of myeloperoxidase (SIEFED).

A more potent inhibitory effect on the MPO myeloperoxidase (SIEFED) activity (FIG. 17).

Figure 18:
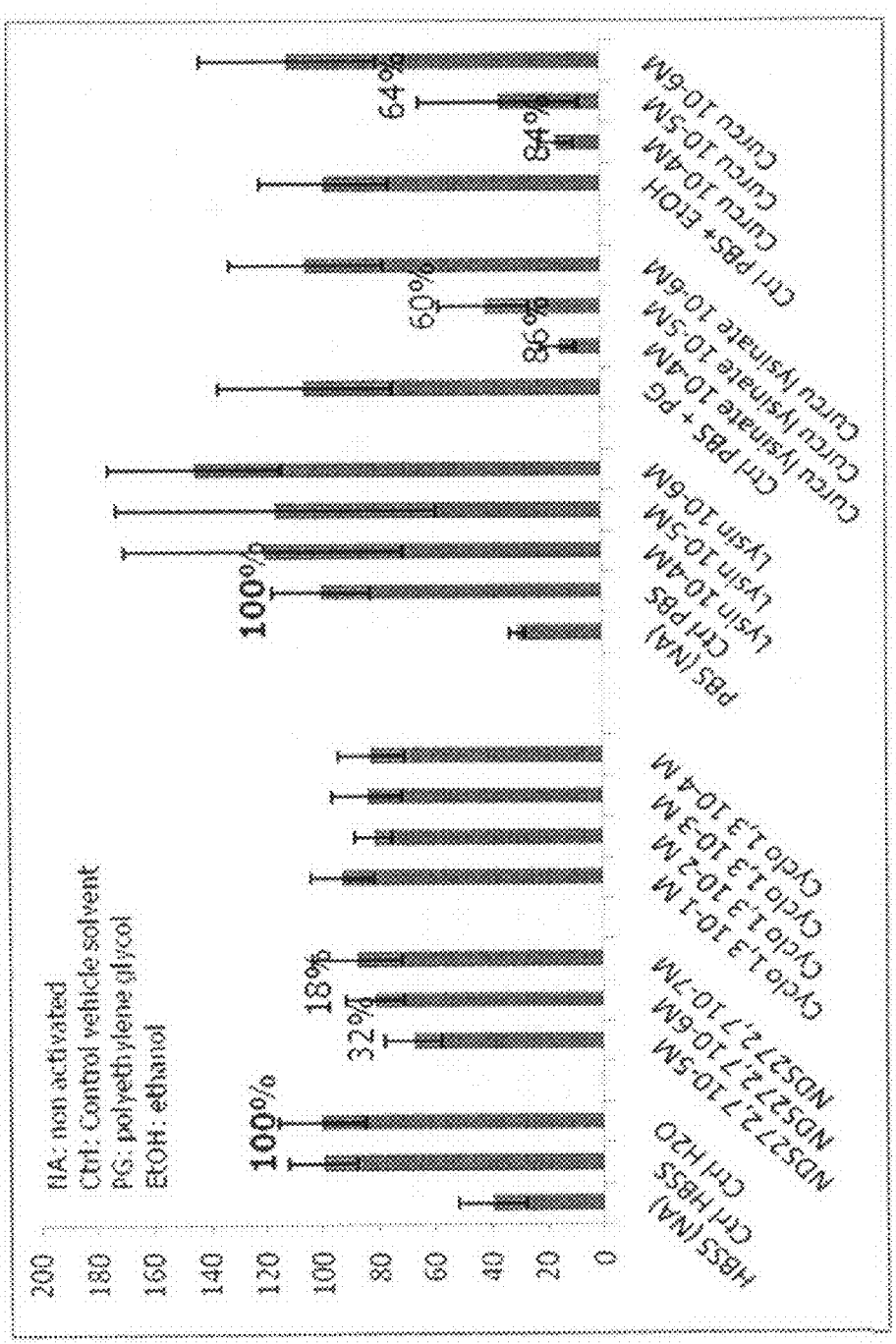
FIG. 18 shows the inhibitory effect on the MPO release by activated neutrophils

A lower effect on the MPO release by the activated neutrophils than curcumin lysinate and pure curcumin (FIG. 18).

Taking into account the improvement of solubility in aqueous medium of the NDS27, these inhibitory effects on the oxidant activity of neutrophils and on MPO activity open therapeutic perspectives in a lot of pathologies with excessive inflammatory reactions in human and equine medicine. The study was performed using the NDS27 composition. However, given the even higher solubility of the NDS28 composition and its identical active ingredient curcumin lysinate, we expect to obtain at least similar results with the NDS28 compound.

What is claimed is:

1. A water soluble curcumin compound for treating proliferative and/or inflammatory disorders, characterised in that the compound is a hydroxypropyl-beta-cyclodextrin complex of curcumin lysinate (NDS27).

2. A pharmaceutical composition comprising at least a therapeutically sufficient amount of the water soluble hydroxypropyl-beta-cyclodextrin complex of curcumin lysinate (NDS27) according to claim 1 as active ingredient and a pharmaceutically acceptable vehicle or carrier.

3. A pharmaceutical composition according to claim 2, wherein the therapeutically sufficient amount is comprised between 0.01 mg and 1000 mg per kilogram of body weight of the individual to which it is administered.

4. A pharmaceutical composition according to claim 2, said pharmaceutical composition having a pharmaceutically acceptable administration form selected from the group consisting of tablets, pills, capsules, suppositories, syrups, solutions, creams, inhalator liquid or powder and sprays.

5. A pharmaceutical composition according to claim 2, further comprising an adjuvant able to increase or regulate humoral and/or cellular response of the immune system against the active principle or against the vehicle or carrier so as to reduce or suppress side-effects or toxic effects associated to the active principle and/or the vehicle or carrier.

6. A method of treating proliferative and/or inflammatory disorders in a subject in need thereof, comprising administering a pharmaceutically acceptable amount of the water soluble hydroxypropyl-beta-cyclodextrin complex of curcumin lysinate (NDS27) according to claim 1.

7. The method of claim 6, wherein the proliferative disorder is neoplasm, dysplasia, premalignant or precancerous lesions, abnormal cell growths, benign tumours, malignant tumours, cancer or metastasis, or wherein said inflammatory disorder is selected from the group of: rheumatoid arthritis, psoriasis, ulcerative colitis, inflammatory diseases of gastro-intestinal tract, central nervous system diseases, atherosclerosis, diabetes, arthritis and graft-versus host diseases, fibromyalgia, asthma, chronic obstructive pulmonary disease (COPD), pneumonia, bronchitis, recurrent airway obstruction (RAO), multiple sclerosis, type-I diabetes, systemic lupus erythematosus, scleroderma, systemic sclerosis, Sjögren's syndrome, autoimmune disorders, chronic inflammation, allergic reactions and hypersensitivities, inflammatory bowel diseases, reperfusion injury and rheumatoid arthritis.

8. The method of claim 6, wherein the patient is a mammal.

9. A method for inhibiting release of Reactive Oxygen Species (ROS) and myeloperoxydase by neutrophils, comprising administering a pharmaceutically active amount of the water soluble hydroxypropyl-beta-cyclodextrin complex of curcumin lysinate (NDS27) according to claim 1.

10. A method for inhibiting release of Reactive Oxygen Species (ROS) and myeloperoxydase by neutrophils, comprising administering a pharmaceutically active amount of the pharmaceutical composition according to claim 2.

11. A method of treating proliferative and/or inflammatory disorders in a subject in need thereof, comprising administering a pharmaceutically acceptable amount of the pharmaceutical composition according to claim 2.

12. The method of claim 11, wherein the proliferative disorder is neoplasm, dysplasia, premalignant or precancerous lesions, abnormal cell growths, benign tumours, malignant tumours, cancer or metastasis, or wherein said inflammatory disorder is selected from the group of: rheumatoid arthritis, psoriasis, ulcerative colitis, inflammatory diseases of gastro-intestinal tract, central nervous system diseases, atherosclerosis, diabetes, arthritis and graft-versus host diseases; fibromyalgia, asthma, chronic obstructive pulmonary disease (COPD), pneumonia, bronchitis, recurrent airway obstruction (RAO), multiple sclerosis, type-I diabetes, systemic lupus erythematosus, scleroderma, systemic sclerosis, Sjögren's syndrome, autoimmune disorders, chronic inflammation, allergic reactions and hypersensitivities, inflammatory bowel diseases, reperfusion injury and rheumatoid arthritis.

13. The method of claim 11, wherein the patient is a mammal.

14. The method of claim 8, wherein the mammal is a human or horse.

15. The method of claim 13, wherein the mammal is a human or horse.

16. A Process for producing a water soluble hydroxypropyl-beta-cyclodextrin complex of curcumin lysinate (NDS27) according to claim 1, comprising the following steps:
 a) synthesis of pure curcumin using standard methodology,
 b) synthesis of salts of curcumin lysinate comprising the steps of:
  (i) dissolving curcumin under heat in methanol (solution 1),
  (ii) dissolving lysine base in water (solution 2), and
  (iii) stirring solution 2 into solution 1, followed by shaking and evaporation under vacuum,
  (iv) redissolving the residue in ethanol and bringing to boiling point,
  (v) filtering out the non-dissolved residue and placing the ethanol based solution at about −20° C. for about one hour,
  (vi) collecting the precipitate of curcumin lysinate,
 c) preparation of cyclodextrin complex of curcumin lysinate comprising the steps of:
  (i) providing an aqueous hydroxypropyl-beta-cyclodextrin (HP-beta-CD) solution,
  (ii) adding curcumin lysinate to the cyclodextrin solution in one movement while stirring well,
  (iii) filtering the resulting solution,
 d) optionally esterifying curcumin resulting in an acylated derivative of curcumin or a derivative thereof or optionally using a glycosylation step.

* * * * *

UNITED STATES PATENT AND TRADEMARK OFFICE
CERTIFICATE OF CORRECTION

PATENT NO.         : 8,772,265 B2
APPLICATION NO.    : 12/995126
DATED              : July 8, 2014
INVENTOR(S)        : Philippe Neven et al.

It is certified that error appears in the above-identified patent and that said Letters Patent is hereby corrected as shown below:

On Title Page 1 (item 57, Abstract) at line 11, Change "cucumin" to --curcumin--.

In the Specification

In column 6 at lines 53-54, Change "chemiluminekence." to --chemiluminescence.--.

In column 6 at line 58, Change "neutrophils" to --neutrophils.--.

In column 7 at line 16 (approx.), Change "alkoxy" to --alkoxy.--.

In column 8 at line 34, Change "Cyclodextrines" to --Cyclodextrins--.

In column 8 at line 64, Change "increased)" to --increased).--.

In column 11 at line 9, Change "vulval" to --vulvar--.

In column 13 at line 34, Change "dysplasia. epiphysialis" to --dysplasia epiphysialis--.

In column 14 at line 3, Change "ependymonas." to --ependymomas.--.

In column 15 at line 29, Change "orang-utans," to --orangutans,--.

In column 20 at line 17, Change "intra-stemal" to --intra-sternal--.

In column 23 at line 27, Change "Post surgical" to --Post-surgical--.

In column 24 at line 66, Change "choloroform-methanol" to --chloroform-methanol--.

In column 27 at line 51 (approx.), Change "Lysinat" to --Lysinate--.

In column 27 at line 52 (approx.), Change "choloroform-methanol" to --chloroform-methanol--.

In column 31 at line 61, Change "250 g" to --250 g.--.

In column 36 at line 12 (approx.), Change "investigated" to --investigated.--.

In column 39 at line 19 (approx.), Change "availablility" to --availability--.

In columns 39-40 (Table 8) at line 3 (approx.), Change "4 °C and at -20 °C" to --4 °C or at -20 °C--.

In column 42 at line 47, Change "(Thermoelectrocorporation," to --(Thermoelectroncorporation,--.

In column 46 at line 52, Change "cucumin" to --curcumin--.

Signed and Sealed this
Seventeenth Day of February, 2015

Michelle K. Lee
*Deputy Director of the United States Patent and Trademark Office*